(12) United States Patent
Schaub et al.

(10) Patent No.: US 8,946,462 B2
(45) Date of Patent: Feb. 3, 2015

(54) PROCESS FOR PREPARING FORMIC ACID BY REACTION OF CARBON DIOXIDE WITH HYDROGEN

(71) Applicant: BASF SE, Ludwigshafen (DE)

(72) Inventors: Thomas Schaub, Neustadt (DE); Marek Pazicky, Heidelberg (DE); Donata Maria Fries, Mannheim (DE); Rocco Paciello, Bad Dürkheim (DE); Anton Meier, Birkenheide (DE)

(73) Assignee: BASF SE (DE)

( * ) Notice: Subject to any disclaimer, the term of this patent is extended or adjusted under 35 U.S.C. 154(b) by 141 days.

(21) Appl. No.: 13/672,055

(22) Filed: Nov. 8, 2012

(65) Prior Publication Data

US 2013/0123526 A1    May 16, 2013

Related U.S. Application Data

(60) Provisional application No. 61/557,931, filed on Nov. 10, 2011.

(51) Int. Cl.

| | |
|---|---|
| *C07F 15/00* | (2006.01) |
| *C07C 53/00* | (2006.01) |
| *C07C 51/15* | (2006.01) |
| *B01J 31/24* | (2006.01) |
| *C07C 51/02* | (2006.01) |
| *C07C 51/41* | (2006.01) |
| *C07C 51/44* | (2006.01) |
| *C07C 51/48* | (2006.01) |

(52) U.S. Cl.
CPC ............... *C07C 51/15* (2013.01); *B01J 31/24* (2013.01); *C07C 51/02* (2013.01); *C07C 51/41* (2013.01); *C07C 51/44* (2013.01); *C07C 51/48* (2013.01)
USPC .............................................. 556/18; 562/609

(58) Field of Classification Search
CPC ....... C07F 15/0053; C07C 51/15; B01J 31/24
USPC ........................................... 556/18; 562/609
See application file for complete search history.

(56) References Cited

U.S. PATENT DOCUMENTS

| | | |
|---|---|---|
| 7,420,088 B2 | 9/2008 | Karl et al. |
| 2010/0331573 A1 | 12/2010 | Schaub et al. |

FOREIGN PATENT DOCUMENTS

| | | |
|---|---|---|
| EP | 0181078 B2 | 9/1994 |
| WO | WO-2006/021411 A1 | 3/2006 |
| WO | WO-2010149507 A3 | 3/2011 |
| WO | PCT/EP2011/060012 | 6/2011 |
| WO | PCT/EP2011/060269 | 6/2011 |
| WO | PCT/EP2011/060770 | 6/2011 |
| WO | PCT/EP2011/065810 | 9/2011 |
| WO | PCT/EP2011/072945 | 12/2011 |
| WO | PCT/EP2012/062518 | 6/2012 |
| WO | PCT/EP2012/069458 | 10/2012 |

OTHER PUBLICATIONS

Tzschucke et al., Eur. J. Org. Chem., pp. 5248-5261 (2005).*
Lindner et al., Journal of Organometallic Chemistry, vol. 602, pp. 173-187 (2000).*
U.S. Appl. No. 61/316,841, filed Mar. 24, 2010, BASF SE.
U.S. Appl. No. 61/392,062, filed Oct. 12, 2010, BASF SE.
U.S. Appl. No. 61/512,023.
U.S. Appl. No. 61/532,579.
U.S. Appl. No. 61/544,291.
U.S. Appl. No. 61/545,608.
U.S. Appl. No. 61/557,947.
U.S. Appl. No. 13/172,123.
U.S. Appl. No. 13/171,928.
U.S. Appl. No. 13/234,549.
U.S. Appl. No. 13/171,598.
U.S. Appl. No. 13/330,974.
U.S. Appl. No. 13/542,791.
U.S. Appl. No. 13/559,011.
Henkel, K-D., et al., "Reactor Types and Their Industrial Applications", in Ullmann's Encyklopeida of Industrial Chemistry, (2005), Wiley-VCH Verhalg GmbH & Co. KGaA, Chapter 3.3 "Reactors for gas-liquid reactions", p. 303.
Lewis, J., et al., "Synthesis and Characterisation of a Bulky Chelating bis(phosphine) Ligand, 1,2-bis(di$^n$butylphosphino)ethane (DBPE), and its Iron Metal Coordinated Complexes, Fe(DBPE)$_2$Cl$_2$ and FE(DBPD)$_2$(–C=C–$C_6H_5$)$_2$", Journal of Organometallic Chemistry, vol. 433, (1992), pp. 135-139.
Miller, W. K., et al., "Precursors to Water-Soluble Dinitrogen Carriers. Synthesis of Water-Soluble Complexes of Iron(II) containing Water-Soluble Chelating Phosphine Ligands of the Type 1,2-Bis(bis(hydroxyalkyl)phosphino)ethane", Inorganic Chemistry, vol. 41, No. 21, (2002), pp. 5453-5465.
Müller, E., et al., "Liquid-Liquid Extraction", in Ullmann's Encyklopedia of Industrial Chemistry, (2005), Wiley-VCH Verhalg GmbH & Co., KGaA, Chapter 3, "Apparatus", p. 267.

* cited by examiner

*Primary Examiner* — Porfirio Nazario Gonzalez
(74) *Attorney, Agent, or Firm* — Drinker Biddle & Reath LLP

(57) ABSTRACT

The invention relates to a process for preparing formic acid by reaction of carbon dioxide with hydrogen in a hydrogenation reactor in the presence of a transition metal complex as a catalyst comprising at least one element from group 8, 9 or 10 of the Periodic Table and at least one phosphine ligand with at least one organic radical having at least 13 carbon atoms, of a tertiary amine and of a polar solvent to form a formic acid-amine, adduct, which is subsequently dissociated thermally to formic acid and the corresponding tertiary amine. on unit.

16 Claims, 1 Drawing Sheet

PROCESS FOR PREPARING FORMIC ACID BY REACTION OF CARBON DIOXIDE WITH HYDROGEN

Figure 1:
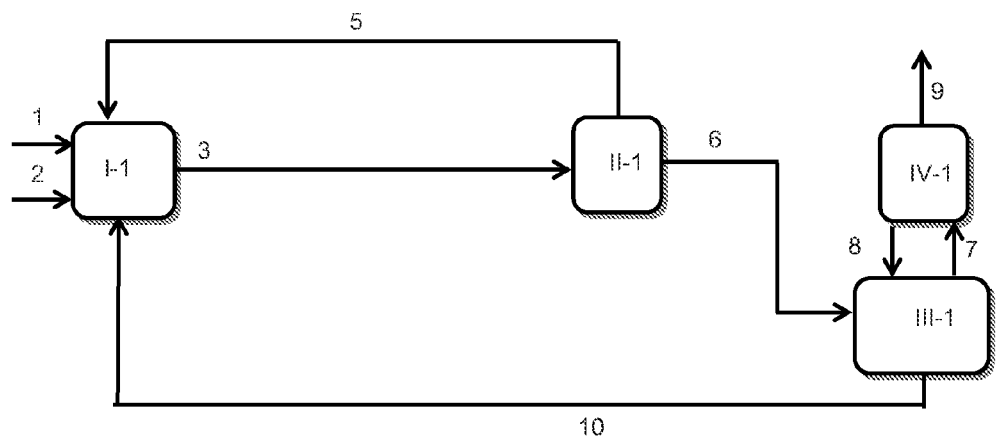

This patent application claims the benefit of pending U.S. provisional patent application Ser. No. 61/557,931 filed Nov. 10, 2011, incorporated in its entirety herein by reference.

The invention relates to a process for preparing formic acid by reaction of carbon dioxide with hydrogen in a hydrogenation reactor in the presence of a transition metal complex as a catalyst comprising at least one element from group 8, 9 or 10 of the Periodic Table and at least one phosphine ligand with at least one organic radical having at least 13 carbon atoms, of a tertiary amine and of a polar solvent to form a formic acid-amine adduct, which is subsequently dissociated thermally to formic acid and the corresponding tertiary amine.

Adducts of formic acid and tertiary amines can be dissociated thermally to free formic acid and tertiary amine, and therefore serve as intermediates in the preparation of formic acid.

Formic acid is an important and versatile product. It is used, for example, for acidification in the production of animal feeds, as a preservative, as a disinfectant, as an auxiliary in the textile and leather industry, as a mixture with salts thereof for deicing of vehicles and runways for takeoff and landing, and as a synthesis unit in the chemical industry.

Said adducts of formic acid and tertiary amines can be prepared in various ways, for example (i) by direct reaction of the tertiary amine with formic acid, (ii) by hydrolysis of methyl formate to formic acid in the presence of the tertiary amine, (iii) by catalytic hydration of carbon monoxide in the presence of the tertiary amine or (iv) by hydrogenation of carbon dioxide to formic acid in the presence of the tertiary amine. The latter process for catalytic hydrogenation of carbon dioxide has the particular advantage that carbon dioxide is available in large volumes and is flexible with regard to its source.

WO 2010/149507 describes a process for preparing formic acid by hydrogenation of carbon dioxide in the presence of a tertiary amine, of a transition metal catalyst and of a high-boiling polar solvent having an electrostatic factor $\geq 200 \ast 10^{-30}$ Cm, for example ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol. A reaction mixture is obtained which comprises the formic acid-amine adduct, the tertiary amine, the high-boiling polar solvent and the catalyst. The reaction mixture is worked up according to WO 2010/149507 by the following steps:

1) phase separation of the reaction mixture to obtain an upper phase comprising the tertiary amine and the catalyst, and a lower phase comprising the formic acid-amine adduct, the high-boiling polar solvent and residues of the catalyst; recycling of the upper phase to the hydrogenation,
2) extraction of the lower phase with the tertiary amine to obtain an extract comprising the tertiary amine and the residues of the catalyst, and a raffinate comprising the high-boiling polar solvent and the formic acid-amine adduct; recycling of the extract to the hydrogenation,
3) thermal dissociation of the raffinate in a distillation column to obtain a distillate comprising the formic acid and a bottoms mixture comprising the free tertiary amine and the high-boiling polar solvent; recycling of the high-boiling polar solvent to the hydrogenation.

A disadvantage of the process of WO 2010/149507 is that the removal of the catalyst is incomplete in spite of phase separation (step 1)) and extraction (step 2)), and so catalyst traces present in the raffinate, in the course of thermal dissociation in the distillation column in step 3), can catalyze the redissociation of the formic acid-amine adduct to carbon dioxide and hydrogen and the tertiary amine according to the following equation:

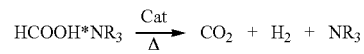

The redissociation leads to a distinct decrease in the yield of adduct of formic acid and tertiary amine, and hence to a decrease in the yield of the formic acid target product.

A further disadvantage is that, in the course of thermal dissociation of the formic acid-amine adduct in the distillation column, there is esterification of the formic acid formed with the high-boiling polar solvents (diols and polyols). This leads to a further reduction in the yield of the formic acid target product.

It is an object of the present invention to provide a process for preparing formic acid by hydrogenation of carbon dioxide, with which substantially complete removal of the catalyst is enabled. The novel process shall have said disadvantages of the prior art only to a distinctly reduced degree, if at all, and lead to concentrated formic acid in high yield and high purity. In addition, the process shall allow a simpler process regime than that described in the prior art, more particularly a simpler process design for workup of the output from the hydrogenation reactor, simpler process stages, a smaller number of process stages or simpler apparatus. In addition, it shall also be possible to perform the process with a very low energy requirement.

The object is achieved by a process for preparing formic acid, comprising the steps of (a) homogeneously catalyzed reaction of a reaction mixture (Rg) comprising carbon dioxide, hydrogen, at least one polar solvent selected from the group consisting of methanol, ethanol, 1-propanol, 2-propanol, 1-butanol, 2-butanol, 2-methyl-1-propanol and water, and a tertiary amine of the general formula (A1)

in which $R^1$, $R^2$, $R^3$ are each independently an unbranched or branched, acyclic or cyclic, aliphatic, araliphatic or aromatic radical having in each case 1 to 16 carbon atoms, where individual carbon atoms may each independently also be substituted by a hetero group selected from the —O— and >N— groups, and two or all three radicals may also be joined to one another to form a chain comprising at least four atoms in each case, in the presence of at least one transition metal complex as a catalyst, comprising at least one element selected from groups 8, 9 and 10 of the Periodic Table and at least one phosphine ligand with at least one organic radical having at least 13 carbon atoms, in a hydrogenation reactor to obtain, optionally after addition of water, a biphasic hydrogenation mixture (H) comprising an upper phase (U1) comprising the catalyst and the tertiary amine (A1), and a lower phase (L1) comprising the at least one polar solvent, residues of the catalyst and a formic acid-amine adduct of the general formula (A2)

$NR^1R^2R^3 * x_i HCOOH$ (A2)

in which
$x_i$ is in the range from 0.4 to 5 and
$R^1$, $R^2$, $R^3$ are each as defined above,
(b) workup of the hydrogenation mixture (H) obtained in step (a) according to one of the following steps:
(b1) phase separation of the hydrogenation mixture (H) obtained in step (a) in a first phase separation apparatus into the upper phase (U1) and the lower phase (L1),
or
(b2) extraction of the catalyst from the hydrogenation mixture (H) obtained in step (a) in an extraction unit with an extractant comprising a tertiary amine (A1) to obtain
a raffinate (R1) comprising the formic acid-amine adduct (A2) and the at least one polar solvent and
an extract (E1) comprising the tertiary amine (A1) and the catalyst
or
(b3) phase separation of the hydrogenation mixture (H) obtained in step (a) in a first phase separation apparatus into the upper phase (U1) and the lower phase (L1) and extraction of the residues of the catalyst from the lower phase (L1) in an extraction unit with an extractant comprising a tertiary amine (A1) to obtain
a raffinate (R2) comprising the formic acid-amine adduct (A2) and the at least one polar solvent and
an extract (E2) comprising the tertiary amine (A1) and the residues of the catalyst,
(c) separation of the at least one polar solvent from the lower phase (L1), from the raffinate (R1) or from the raffinate (R2) in a first distillation apparatus to obtain
a distillate (D1) comprising the at least one polar solvent, which is recycled into the hydrogenation reactor in step (a), and
a biphasic bottoms mixture (B1) comprising
an upper phase (U2) comprising the tertiary amine (A1),
lower phase (L2) comprising the formic acid-amine adduct (A2),
(d) optional workup of the bottoms mixture (B1) obtained in step (c) by phase separation in a second phase separation apparatus into the upper phase (U2) and the lower phase (L2),
(e) dissociation of the formic acid-amine adduct (A2) present in the bottoms mixture (B1) and/or possibly in the lower phase (L2) in a thermal dissociation unit to obtain the corresponding tertiary amine (A1), which is recycled to the hydrogenation reactor in step (a), and formic acid, which is discharged from the thermal dissociation unit.

It has been found that formic acid is obtainable in high yield by the process according to the invention. The process according to the invention enables more effective removal of the transition metal complex used as the catalyst compared to the prior art, and the recycling thereof into the hydrogenation reactor in step (a). This very substantially prevents the redissociation of the formic acid-amine adduct (A2), which leads to an increase in the formic acid yield. The removal of the polar solvent used in accordance with the invention additionally prevents esterification of the formic acid obtained in the thermal dissociation unit in step (e), which likewise leads to a rise in the formic acid yield. In addition, it has been found that, surprisingly, the use of the inventive polar solvent leads to an increase in the concentration of the formic acid-amine adduct (A2) in the hydrogenation mixture (H) obtained in step (a)—compared to the high-boiling polar solvents used in WO2010/149507. This enables the use of smaller reactors, which in turn leads to a cost saving.

The terms "step" and "process stage" are used synonymously hereinafter.

Preparation of the Formic Acid-Amine Adduct (A2); Process Stage (a)

In the process according to the invention, in process stage (a), in a hydrogenation reactor, there is conversion of a reaction mixture (Rg) comprising carbon dioxide, hydrogen, at least one polar solvent selected from the group consisting of methanol, ethanol, 1-propanol, 1-butanol, 2-butanol, 2-methyl-1-propanol and water, and a tertiary amine of the general formula (A1). The reaction is effected in the presence of a catalyst. The catalyst used is at least one transition metal complex comprising at least one element selected from groups 8, 9 and 10 of the Periodic Table and at least one phosphine ligand having at least 13 carbon atoms.

The carbon dioxide used in process stage (a) may be solid, liquid or gaseous. It is also possible to use gas mixtures which comprise carbon dioxide and are available on the industrial scale, provided that they are substantially free of carbon monoxide (proportion by volume of <1% CO). The hydrogen used in the hydrogenation of carbon dioxide in process stage (a) is generally gaseous. Carbon dioxide and hydrogen may also comprise inert gases, for instance nitrogen or noble gases. Advantageously, however, the content thereof is below 10 mol %, based on the total amount of carbon dioxide and hydrogen in the hydrogenation reactor. Larger amounts may likewise still be tolerable in some cases, but generally cause the employment of a higher pressure in the reactor, the result of which is that further compression energy is required.

Carbon dioxide and hydrogen can be fed to process stage (a) as separate streams. It is also possible to use a mixture comprising carbon dioxide and hydrogen in process stage (a).

In the process according to the invention, in process stage (a), at least one tertiary amine (A1) is used in the hydrogenation of carbon dioxide. In the context of the present invention, "tertiary amine (A1)" is understood to mean either one (1) tertiary amine (A1) or mixtures of two or more tertiary amines (A1).

The tertiary amine (A1) used in the process according to the invention is preferably selected such that or matched to the polar solvent such that the hydrogenation mixture (H) obtained in process stage (a), optionally after addition of water, is at least biphasic. The hydrogenation mixture (H) comprises an upper phase (U1), which comprises the catalyst and the tertiary amine (A1), and a lower phase (L1), which comprises the at least one polar solvent, residues of the catalyst and a formic acid-amine adduct (A2).

The tertiary amine (A1) is present enriched in the upper phase (U1), which means that the upper phase (U1) comprises the majority of the tertiary amine (A1), "Enriched" or "majority" with regard to the tertiary amine (A1) should be understood in the context of the present invention to mean a proportion by weight of the free tertiary amine (A1) in the upper phase (U1) of >50% based on the total weight of the free tertiary amine (A1) in the liquid phases, i.e. the upper phase (U1) and the lower phase (L1) in the hydrogenation mixture (H).

Free tertiary amine (A1) is understood to mean the tertiary amine (A1) not bound in the form of the formic acid-amine adduct (A2).

Preferably, the proportion by weight of the free tertiary amine (A1) in the upper phase (U1) is >70%, especially >90%, based in each case on the total weight of the free tertiary amine (A1) in the upper phase (U1) and the lower phase (L1) in the hydrogenation mixture (H).

The tertiary amine (A1) is generally selected by a simple test in which the phase behavior and the solubility of the tertiary amine (A1) in the liquid phases (upper phase (U1) and lower phase (L1)) is determined experimentally under the process conditions in process stage (a). It is additionally possible to add nonpolar solvents to the tertiary amine (A1), for example aliphatic, aromatic or araliphatic solvents. Preferred nonpolar solvents are, for example, octane, toluene and/or xylenes (o-xylene, m-xylene, p-xylene).

Preference is given to tertiary amine of the general formula (A1) in which the $R^1$, $R^2$, $R^3$ radicals are the same or different and each independently an unbranched or branched, acyclic or cyclic, aliphatic, araliphatic or aromatic radical having in each case 1 to 16 carbon atoms, preferably 1 to 12 carbon atoms, where individual carbon atoms may each independently also be substituted by a hetero group selected from the —O— and >N— groups, and two or all three radicals may also be joined to one another to form a chain comprising at least four atoms in each case. In a particularly preferred embodiment, a tertiary amine of the general formula (A1) is used, with the proviso that the total number of carbon atoms is at least 9.

Examples of suitable tertiary amines (A1) include:
tri-n-propylamine, tri-n-butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine.
dimethyldecylamine, dimethyldodecylamine, dimethyltetradecylamine, ethyldi(2-propyl)amine, dioctylmethylamine, dihexylmethylamine.
tricyclopentylamine, tricyclohexylamine, tricycloheptylamine, tricyclooctylamine, and the derivatives thereof substituted by one or more methyl, ethyl, 1-propyl, 2-propyl, 1-butyl, 2-butyl or 2-methyl-2-propyl groups.
dimethylcyclohexylamine, methyldicyclohexylamine, diethylcyclohexylamine, ethyldicyclohexylamine, dimethylcyclopentylamine, methyldicyclopentylamine.
triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis(2-ethylhexyl)phenylamine, tribenzylamine, methyldibenzylamine, ethyldibenzylamine, and the derivatives thereof substituted by one or more methyl, ethyl, 1-propyl, 2-propyl, 1-butyl, 2-butyl or 2-methyl-2-propyl groups.
N—$C_1$— to —$C_{12}$-alkylpiperidines, N,N-di-$C_1$— to —$C_{12}$-alkylpiperazines, N—$C_1$— to —$C_{12}$-alkylpyrrolidones, N—$C_1$— to —$C_{12}$-alkylimidazoles, and the derivatives thereof substituted by one or more methyl, ethyl, 1-propyl, 2-propyl, 1-butyl, 2-butyl or 2-methyl-2-propyl groups.
1,8-diazabicyclo[5.4.0]undec-7-ene ("DBU"), 1,4-diazabicyclo[2.2.2]octane ("DAB-CO"), N-methyl-8-azabicyclo[3.2.1]octane ("tropane"), N-methyl-9-azabicyclo[3.3.1]nonane ("granatane"), 1-azabicyclo[2.2.2]octane ("quinuclidine").

In the process according to the invention, it is also possible to use mixtures of two or more different tertiary amines (A1).

Especially preferably, the tertiary amine (A1) used in the process according to the invention is an amine in which the $R^1$, $R^2$, $R^3$ radicals are each independently selected from the group of $C_1$ — to $C_{12}$-alkyl, $C_5$— to $C_8$-cycloalkyl, benzyl and phenyl.

Especially preferably, the tertiary amine (A1) used in the process according to the invention is a saturated amine, i.e. an amine comprising only single bonds.

Very especially preferably, the tertiary amine used in the process according to the invention is an amine of the general formula (A1) in which the $R^1$, $R^2$, $R^3$ radicals are each independently selected from the group of $C_5$— to $C_8$-alkyl, especially tri-n-pentylamine, tri-n-hexylamine, tri-n-heptylamine, tri-n-octylamine, dimethylcyclohexylamine, methyldicyclohexylamine, dioctylmethylamine and dimethyldecylamine.

In one embodiment of the process according to the invention, one (1) tertiary amine of the general formula (A1) is used.

More particularly, the tertiary amine used is an amine of the general formula (A1) in which the $R^1$, $R^2$, $R^3$ radicals are each independently selected from $C_5$— and $C_6$-alkyl. Most preferably, the tertiary amine of the general formula (A1) used in the process according to the invention is tri-n-hexylamine.

Preferably, the tertiary amine (A1) in all process stages of the process according to the invention is in liquid form. However, this is not an absolute requirement. It would also be sufficient if the tertiary amine (A1) were at least dissolved in suitable solvents. Suitable solvents are in principle those which are chemically inert with respect to the hydrogenation of carbon dioxide, in which the tertiary amine (A1) and the catalyst are of good solubility, and in which, conversely, the polar solvent and the formic acid-amine adduct (A2) are of sparing solubility. Possible solvents therefore in principle include chemically inert, nonpolar solvents, for instance aliphatic, aromatic or araliphatic hydrocarbons, for example octane and higher alkanes, toluene, xylenes.

In the process according to the invention, in process stage (a), at least one polar solvent selected from the group consisting of methanol, ethanol, 1-propanol, 2-propanol, 1-butanol, 2-butanol, 2-methyl-1-propanol and water is used in the hydrogenation of carbon dioxide.

A "polar solvent" in the context of the present invention is understood to mean either one (1) polar solvent or mixtures of two or more polar solvents.

The polar solvent is preferably selected such that the hydrogenation mixture (H) obtained in process stage (a), optionally after addition of water, is at least biphasic. The polar solvent should be present enriched in the lower phase (L1), i.e. the lower phase (L1) should comprise the majority of the polar solvent. "Enriched" or "majority" with regard to the polar solvent should be understood in the context of the present invention to mean a proportion by weight of the polar solvent in the lower phase (L1) of >50% based on the total weight of the polar solvent in the liquid phases (upper phase (U1) and lower phase (L1)) in the hydrogenation reactor.

Preferably, the proportion by weight of the polar solvent in the lower phase (L1) is >70%, especially >90%, based in each case on the total weight of the polar solvent in the upper phase (U1) and the lower phase (L1).

The polar solvent which fulfills the above criteria is generally selected by a simple test in which the phase behavior and the solubility of the polar solvent in the liquid phases (upper phase (U1) and lower phase (L18 are determined experimentally under the process conditions in process stage (a).

The polar solvent may be a pure polar solvent or a mixture of two or more polar solvents.

In one embodiment of the process according to the invention, in step (a), a monophasic hydrogenation mixture is first obtained, which is converted by the addition of water to the biphasic hydrogenation mixture (H).

In a further embodiment of the process according to the invention, in step (a), the biphasic hydrogenation mixture (H) is obtained directly. The biphasic hydrogenation mixture (H) obtained by this embodiment can be supplied directly to the workup according to step (b). It is also possible to additionally add water to the biphasic hydrogenation mixture (H) before the further workup in step (b). This can lead to an increase in the partition coefficient $P_K$.

In a further particularly preferred embodiment, the polar solvent used is water, methanol or a mixture of water and methanol.

The use of diols and the formic esters thereof, polyols and the formic esters thereof, sulfones, sulfoxides and open-chain or cyclic amides as the polar solvent is not preferred. In a preferred embodiment, these polar solvents are not present in the reaction mixture (Rg).

The molar ratio of the polar solvent or solvent mixture used in process stage (a) in the process according to the invention to the tertiary amine (A1) used is generally 0.5 to 30 and preferably 1 to 20.

The transition metal complex used as the catalyst for hydrogenation of carbon dioxide in process stage (a) in the process according to the invention comprises at least one element selected from groups 8, 9 and 10 of the Periodic Table (IUPAC nomenclature) and at least one phosphine ligand with at least one organic radical having at least 13 carbon atoms. Groups 8, 9 and 10 of the Periodic Table comprise Fe, Co, Ni, Ru, Rh, Pd, Os, Ir and Pt. In process stage (a), the catalyst used may be one (1) transition metal complex or a mixture of two or more transition metal complexes. "Transition metal complex" is understood in the context of the present invention to mean either one (1) transition metal complex or mixture of two or more transition metal complexes.

Preferably, the transition metal complex used as the catalyst comprises at least one element from the group consisting of Ru, Rh, Pd, Os, Ir and Pt, especially preferably at least one element from the group consisting of Ru, Rh and Pd. Very especially preferably, the transition metal complex comprises Ru.

Transition metal complexes preferred as catalysts comprise at least one phosphine ligand with at least one organic radical having 13 to 30 carbon atoms, preferably having 14 to 26 carbon atoms, more preferably having 14 to 22 carbon atoms, especially preferably having 15 to 22 carbon atoms, especially having 16 to 20 carbon atoms, where the organic radical is bonded to a phosphorus atom of the phosphine ligand.

In a further preferred embodiment, the transition metal complexes used as catalysts comprise at least one bidentate phosphine ligand of the general formula (I)

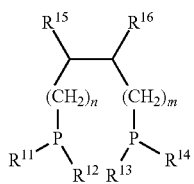

(I)

in which
$R^{11}$, $R^{12}$, $R^{13}$, $R^{14}$ are each independently unsubstituted or at least monosubstituted —$C_{13}$-$C_{30}$-alkyl, -(phenyl)-($C_7$-$C_{24}$-alkyl), -(phenyl)-($C_4$-$C_{24}$-alkyl)$_2$, -(phenyl)-($C_3$-$C_{24}$-alkyl)$_3$, -(phenyl)-(O—$C_7$-$C_{24}$-alkyl), -(phenyl)-(O—$C_4$-$C_{24}$-alkyl)$_2$, -(phenyl)-(O—$C_3$-$C_{24}$-alkyl)$_3$, -(cyclohexyl)-($C_7$-$C_{24}$-alkyl), -(cyclohexyl)-($C_4$-$C_{24}$-alkyl)$_2$, -(cyclohexyl)-($C_3$-$C_{24}$-alkyl)$_3$, -(cyclohexyl)-(O—$C_7$-$C_{24}$-alkyl), -(cyclohexyl)-(O—$C_4$-$C_{24}$-alkyl)$_2$ or -(cyclohexyl)-(O—$C_3$-$C_{24}$-alkyl)$_3$,
where the substituents are selected from the group consisting of —F, —Cl, —Br, —OH, —OR$^a$, —COOH, —COOR$^a$, —OCOR$^a$, —CN, —NH$_2$, —N(R$^a$)$_2$ and —NHR$^a$;
$R^{15}$, $R^{16}$ are each independently hydrogen or —$C_1$-$C_4$-alkyl or, together with the carbon atoms to which they are bonded, form an unsubstituted or at least monosubstituted phenyl or cyclohexyl ring,
where the substituents are selected from the group consisting of —OCOR$^a$, —OCOCF$_3$, —OSO$_2$R$^a$, —OSO$_2$CF$_3$, —CN, —OH, —OR$^a$, —N(R$^a$)$_2$, —NHR$^a$ and —$C_1$-$C_4$-alkyl;
R$^a$ is —$C_1$-$C_4$-alkyl and
n, m are each independently 0, 1 or 2.

—$C_{13}$-$C_{30}$-Alkyl, in relation to the $R^{11}$, $R^{12}$, $R^{13}$ and $R^{14}$ radicals, is understood in the context of the present invention to mean linear or branched alkyl radicals having 13 to 30 carbon atoms. These radicals comprise linear or branched alkyl radicals selected from the group consisting of tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl and triacontyl. The —$C_{13}$-$C_{30}$-alkyl radicals are preferably unbranched, i.e. linear.

Preferred alkyl radicals (—$C_{13}$-$C_{30}$-alkyl) are linear or branched alkyl radicals having 14 to 26 (—$C_{14}$-$C_{26}$-alkyl), more preferably having 14 to 22 (—$C_{14}$-$C_{22}$-alkyl), especially preferably having 15 to 22 (—$C_{15}$-$C_{22}$-alkyl) and especially having 16 to 20 (—$C_{16}$-$C_{20}$-alkyl) carbon atoms, preference being given to linear alkyl radicals.

-(Phenyl)-($C_7$-$C_{24}$-alkyl), in relation to the $R^{11}$, $R^{12}$, $R^{13}$ and $R^{14}$ radicals, is understood in the context of the present invention to mean radicals of the general formula (II) which are bonded via the phenyl ring to the phosphorus atom of the phosphine ligand (I). The —$C_7$-$C_{24}$-alkyl radicals may be bonded to the phenyl ring in the 2, 3 or 4 position and may be linear or branched. The phenyl ring preferably does not bear any further substituents apart from the —$C_7$-$C_{24}$-alkyl radical. The —$C_7$-$C_{24}$-alkyl radicals may be unsubstituted or at least monosubstituted. The —$C_7$-$C_{24}$-alkyl radicals are preferably linear and unsubstituted.

Preferred alkyl radicals in the -(phenyl)-($C_7$-$C_{24}$-alkyl) radical are linear or branched alkyl radicals having 7 to 18 (i.e. -(phenyl)-($C_7$-$C_{18}$-alkyl)). Particular preference is given to alkyl radicals having 7 to 12 carbon atoms (i.e. -(phenyl)-($C_7$-$C_{12}$-alkyl)).

-(Phenyl)-(O—$C_6$-$C_{24}$-alkyl), in relation to the $R^{11}$, $R^{12}$, $R^{13}$ and $R^{14}$ radicals, is understood in the context of the present invention to mean radicals of the general formula (II) which are bonded via the phenyl ring to the phosphorus atom of the phosphine ligand (I). The —O—$C_7$-$C_{24}$-alkyl radicals may be bonded to the phenyl ring via the oxygen in the 2, 3 or 4 position and may be linear or branched. The phenyl ring preferably does not bear any further substituents apart from the —$C_7$-$C_{24}$-alkyl radical. The —O—$C_7$-$C_{24}$-alkyl radicals may be unsubstituted or at least monosubstituted. The —$C_7$-$C_{24}$-alkyl radicals are preferably linear and unsubstituted.

Preferred alkyl radicals in the -(phenyl)-(O—$C_7$-$C_{24}$-alkyl) radical are linear or branched alkyl radicals having 7 to 18 carbon atoms (i.e. -(phenyl)-(O—$C_7$-$C_{18}$-alkyl)). Particular preference is given to alkyl radicals having 7 to 12 carbon atoms (i.e. -(phenyl)-(O—$C_7$-$C_{12}$-alkyl)).

-(Cyclohexyl)-($C_7$-$C_{24}$-alkyl), in relation to the $R^{11}$, $R^{12}$, $R^{13}$ and $R^{14}$ radicals, is understood in the context of the present invention to mean radicals of the general formula (IV) which are bonded via the cyclohexyl ring to the phosphorus atom of the phosphine ligand (I). The —$C_7$-$C_{24}$-alkyl radicals may be bonded to the cyclohexyl ring in the 2, 3 or 4 position and may be linear or branched. The cyclohexyl ring preferably does not bear any further substituents apart from the —$C_7$-$C_{24}$-alkyl radical. The —$C_7$-$C_{24}$-alkyl radicals may be unsubstituted or at least monosubstituted. The —$C_7$-$C_{24}$-alkyl radicals are preferably linear and unsubstituted. Preferred alkyl radicals in the (cyclohexyl)-($C_7$-$C_{24}$-alkyl) radical are linear or branched alkyl radicals having 7 to 18 carbon atoms (i.e. -(cyclohexyl)-($C_7$-$C_{18}$-alkyl)). Particular preference is given to alkyl radicals having 7 to 12 carbon atoms (i.e. -(cyclohexyl)-($C_7$-$C_{12}$-alkyl)).

-(Cyclohexyl)-(O—$C_7$-$C_{24}$-alkyl), in relation to the $R^{11}$, $R^{12}$, $R^{13}$ and $R^{14}$ radicals, is understood in the context of the present invention to mean radicals of the general formula (V) which are bonded via the cyclohexyl ring (wavy bond; 1 position) to the phosphorus atom of the phosphine ligand (I). The —O—$C_7$-$C_{24}$-alkyl radicals are bonded to the cyclohexyl ring via the oxygen in the 2, 3 or 4 position and may be linear or branched. The cyclohexyl ring preferably does not bear any further substituents apart from the —$C_7$-$C_{24}$-alkyl radical. The —O—$C_7$-$C_{24}$-alkyl radicals may be unsubstituted or at least monosubstituted. The —$C_7$-$C_{24}$-alkyl radicals are preferably linear and unsubstituted. Preferred alkyl radicals in the -(cyclohexyl)-(O—$C_7$-$C_{24}$-alkyl) radical are linear or branched alkyl radicals having 7 to 18 carbon atoms (i.e. -(cyclohexyl)-(O—$C_7$-$C_{18}$-alkyl)). Particular preference is given to alkyl radicals having 7 to 12 ca on atoms (i.e. -(cyclohexyl)-(O—$C_7$-$C_{12}$-alkyl)).

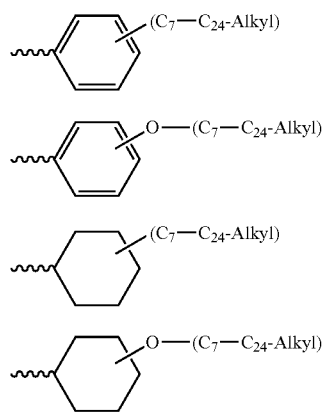

The wavy bond in the formulae II, III, IV and V indicates the bond of the phenyl or cyclohexyl ring to the phosphorus atom of the phosphine ligand (I) (1 position).

In the formulae II, III, IV and V, the —$C_7$-$C_{24}$-alkyl or the —O—$C_7$-$C_{24}$-alkyl radicals are bonded to the phenyl rings or the cyclohexyl rings preferably in the 4 position. The phenyl rings or cyclohexyl rings preferably bear, in the 4 position, a —$C_7$-$C_{18}$-alkyl or —O—$C_7$-$C_{18}$-alkyl radical. The phenyl rings or cyclohexyl rings especially preferably bear, in the 4 position, a —$C_7$-$C_{12}$-alkyl or —O—$C_7$-$C_{12}$-alkyl radical.

-(Phenyl)-($C_4$-$C_{24}$-alkyl)$_2$, in relation to the $R^{11}$, $R^{12}$, $R^{13}$ and $R^{14}$ radicals, is understood in the context of the present invention to mean radicals which are bonded via the phenyl ring to the phosphorus atom of the phosphine ligand (I) and the phenyl ring bears two —$C_4$-$C_{24}$-alkyl radicals. The —$C_4$-$C_{24}$-alkyl radicals may be bonded to the phenyl ring in the (2,3), (2,4), (2,5), (2,6), (3,4) or (3,5) positions, preference being given to the (3,5) position. The —$C_4$-$C_{24}$-alkyl radicals may be linear or branched. The phenyl ring preferably does not bear any further substituents apart from the two —$C_4$-$C_{24}$-alkyl radicals. The —$C_4$-$C_{24}$-alkyl radicals may be unsubstituted or at least monosubstituted. The —$C_4$-$C_{24}$-alkyl radicals are preferably unsubstituted.

Preferred alkyl radicals in the -(phenyl)-($C_4$-$C_{24}$-alkyl)$_2$ radical are linear or branched alkyl radicals having 4 to 18 (i.e. -(phenyl)-($C_4$-$C_{18}$-alkyl))$_2$. Particular preference is given to alkyl radicals having 4 to 12 carbon atoms (i.e. -(phenyl)-($C_4$-$C_{12}$-alkyl))$_2$ and especially having 4 to 6 carbon atoms (i.e. -(phenyl)-($C_4$-$C_6$-alkyl))$_2$. An example of a suitable alkyl radical is tert-butyl.

-(Phenyl)-(O—$C_4$-$C_{24}$-alkyl)$_2$, in relation to the $R^{11}$, $R^{12}$, $R^{13}$ and $R^{14}$ radicals, is understood in the context of the present invention to mean radicals which are bonded via the phenyl ring to the phosphorus atom of the phosphine ligand (I) and the phenyl ring bears two —O—$C_4$-$C_{24}$-alkyl radicals. The —O—$C_4$-$C_{24}$-alkyl radicals may be bonded to the phenyl ring in the (2,3), (2,4), (2,5), (2,6), (3,4) or (3,5) positions, preference being given to the (3,5) position. The —O—$C_4$-$C_{24}$-alkyl radicals may be linear or branched. The phenyl ring preferably does not bear any further substituents apart from the two —O—$C_4$-$C_{24}$-alkyl radicals. The —O—$C_4$-$C_{24}$-alkyl radicals may be unsubstituted or at least monosubstituted. The —O—$C_4$-$C_{24}$-alkyl radicals are preferably unsubstituted.

Preferred alkyl radicals in the -(phenyl)-(O—$C_4$-$C_{24}$-alkyl)$_2$ radical are linear or branched alkyl radicals having 4 to 18 (i.e. -(phenyl)-(O—$C_4$-$C_{18}$-alkyl))$_2$. Particular preference is given to alkyl radicals having 4 to 12 carbon atoms (i.e. -(phenyl)-(O—$C_4$-$C_{12}$-alkyl))$_2$ and especially having 4 to 6 carbon atoms (i.e. -(phenyl)-(O—$C_4$-$C_6$-alkyl))$_2$. An example of a suitable —O-alkyl radical is tert-butoxy.

For -(cyclohexyl)-($C_4$-$C_{24}$-alkyl)$_2$ and -(cyclohexyl)-(O—$C_4$-$C_{24}$-alkyl)$_2$, the above details and preferences for -(phenyl)-($C_4$-$C_{24}$-alkyl)$_2$ and -(phenyl)-(O—$C_4$-$C_{24}$-alkyl)$_2$ apply correspondingly.

-(Phenyl)-($C_3$-$C_{24}$-alkyl)$_3$, -(phenyl)-(O—$C_3$-$C_{24}$-alkyl)$_3$, -(cyclohexyl)-($C_3$-$C_{24}$-alkyl)$_3$, -(cyclohexyl)-(O—$C_3$-$C_{24}$-alkyl) and -(cyclohexyl)-(O—$C_3$-$C_{24}$-alkyl)$_3$ are understood to mean phenyl and cyclohexyl rings which are bonded to the phosphorus atom of the phosphine ligand (I) in the 1 position, the phenyl or cyclohexyl ring bearing three —$C_3$-$C_{24}$-alkyl radicals or three —O—$C_3$-$C_{24}$-alkyl radicals. The —$C_3$-$C_{24}$-alkyl —O—$C_3$-$C_{24}$-alkyl radicals may be bonded to the phenyl or cyclohexyl ring in the (2,3,4), (2,3,5), (2,4,6), (3,4,5) or (2,3,6) positions.

Particular preference is given to phosphine ligands (I) in which the $R^{11}$, $R^{12}$, $R^{13}$ and $R^{14}$ radicals are the same.

Particular preference is further given to phosphine ligands of the general formula (I) in which $R^{11}$, $R^{12}$, $R^{13}$, $R^{14}$ are each independently unsubstituted or at least monosubstituted —$C_{13}$-$C_{30}$-alkyl, -(phenyl)-($C_7$-$C_{24}$-alkyl), -(phenyl)-($C_4$-$C_{24}$-alkyl)$_2$, -(phenyl)-(O—$C_7$-$C_{24}$-alkyl), -(phenyl)-(O—$C_4$-$C_{24}$-alkyl)$_2$, -(cyclohexyl)-

($C_7$-$C_{24}$-alkyl), -(cyclohexyl)-($C_4$-$C_{24}$-alkyl)$_2$, -(cyclohexyl)-(O—$C_7$-$C_{24}$-alkyl) or -(cyclohexyl)-(O—$C_4$-$C_{24}$-alkyl)$_2$, where the substituents are selected from the group consisting of —F, —Cl, —Br, —OH, —OR$^a$, —COOH, —COOR$^a$, —OCOR$^a$, —CN, —NH$_2$, —N(R$^a$)$_2$ and —NHR$^a$;

$R^{15}$, $R^{16}$ are each independently hydrogen or —$C_1$-$C_4$-alkyl or, together with the carbon atoms to which they are bonded, form an unsubstituted or at least monosubstituted phenyl or cyclohexyl ring, where the substituents are selected from the group consisting of —OCOR$^a$, —OCOCF$_3$, —OSO$_2$R$^a$, —OSO$_2$CF$_3$, —CN, —OH, —OR$^a$, —N(R$^a$)$_2$, —NHR$^a$ and —$C_1$-$C_4$-alkyl;

R$^a$ is —$C_1$-$C_4$-alkyl and n, m are both 0, 1 or 2, preferably both 0 or 1, especially both 0.

Particular preference is further given to phosphine ligands of the general formula (I) in which $R^{11}$, $R^{12}$, $R^{13}$, $R^{14}$ are each independently unsubstituted or at least monosubstituted —$C_{13}$-$C_{30}$-alkyl, -(phenyl)-($C_7$-$C_{24}$-alkyl), -(phenyl)-(O—$C_7$-$C_{24}$-alkyl), -(cyclohexyl)-($C_7$-$C_{24}$-alkyl) or -(cyclohexyl)-(O—$C_7$-$C_{24}$-alkyl), where the substituents are selected from the group consisting of —F, —Cl, —Br, —OH, —OR$^a$, —COOH, —COOR$^a$, —OCOR$^a$, —CN, —NH$_2$, —N(R$^a$)$_2$ and —NHR$^a$;

$R^{15}$, $R^{16}$ are each independently hydrogen or —$C_1$-$C_4$-alkyl or, together with the carbon atoms to which they are bonded, form an unsubstituted or at least monosubstituted phenyl or cyclohexyl ring, where the substituents are selected from the group consisting of —OCOR$^a$, —OCOCF$_3$, —OSO$_2$R$^a$, —OSO$_2$CF$_3$, —CN, —OH, —OR$^a$, —N(R$^a$)$_2$, —NHR$^a$ and —$C_1$-$C_4$-alkyl;

R$^a$ is —$C_1$-$C_4$-alkyl and n, m are both 0, 1 or 2, preferably both 0 or 1, especially both 0.

Particular preference is further given to phosphine ligands of the general formula (I) in which $R^{11}$, $R^{12}$, $R^{13}$, $R^{14}$ are each independently unsubstituted or at least monosubstituted —$C_{13}$-$C_{30}$-alkyl, where the substituents are selected from the group consisting of —F, —Cl, —Br, —OH, —OR$^a$, —COOH, —COOR$^a$, —OCOR$^a$, —CN, —NH$_2$, —N(R$^a$)$_2$ and —NHR$^a$;

$R^{15}$, $R^{16}$ are each independently hydrogen or —$C_1$-$C_4$-alkyl,

R$^a$ is —$C_1$-$C_4$-alkyl and n, m are both 0.

More preferred are phosphine ligands of the general formula (I) in which $R^{11}$, $R^{12}$, $R^{13}$, $R^{14}$ are each independently unsubstituted —$C_{13}$-$C_{30}$-alkyl;

$R^{15}$, $R^{16}$ are both hydrogen and n, m are both 0.

Most preferred are phosphine ligands of the general formula (I) in which $R^{11}$, $R^{12}$, $R^{13}$, $R^{14}$ are all unsubstituted —$C_{12}$-$C_{20}$-alkyl, preferably unsubstituted $C_{12}$-$C_{18}$-alkyl and more preferably $C_{13}$-$C_{18}$-alkyl;

$R^{15}$, $R^{16}$ are both hydrogen and n, m are both 0.

Particularly preferred bidentate phosphine ligands (I) are selected from the group consisting of 1,2-bis(ditetradecylphosphino)ethane, 1,2-bis(dipentadecylphosphino) ethane, 1,2-bis(dihexadecylphosphino)ethane, and 1,2-bis(dioctadecylphosphino)ethane.

Phosphine ligands of the general formula (I) in which n and m are both 0 are obtainable, for example, by reaction of 1,2-bis(dichlorophosphino)ethane compounds of the general formula (VIII) with Grignard compounds of the general formula (IX) according to the following reaction equation 1 (RE 1), where R$^{17}$ in the formulae (IX) and (I) is as defined above for $R^{11}$, $R^{12}$, $R^{13}$, $R^{14}$, the preferences applying correspondingly. For $R^{15}$ and $R^{16}$ in formula (VIII), the definitions and preferences given for the phosphine ligand (I) apply correspondingly.

RE 1

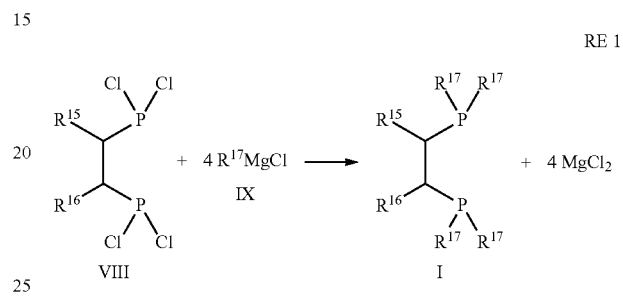

The general reaction of 1,2-bis(dichlorophosphino)ethane with a butyl Grignard compound is described in Jack Lewis, et al. Journal of Organometallic Chemistry, 433 (1992), 135-139.

Phosphine ligands of the general formula (I) in which n and m are both 0 and in which $R^{11}$, $R^{12}$, $R^{13}$ and $R^{14}$ are each independently unsubstituted or at least monosubstituted —$C_{12}$-$C_{30}$-alkyl are additionally obtainable, for example, by reaction of 1,2-bis(dihydrophosphino)ethane compounds of the general formula (X) with terminal olefins of the general formula (XI) according to the following reaction equation 2 (RE 2), where, for $R^{18}$ in the formulae (XI) and (I), the definitions and preferences given above for $R^{11}$, $R^{12}$, $R^{13}$, $R^{14}$ apply analogously. For $R^{15}$ and $R^{16}$ in formula (X), the definitions and preferences given for the phosphine ligand (I) apply correspondingly.

RE 2

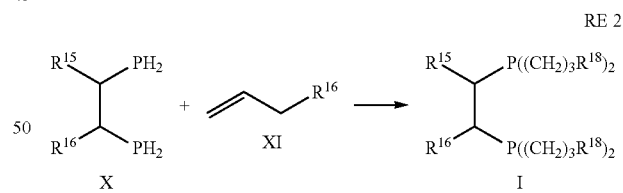

The general reaction of 1,2-bis(dihydrophosphino)ethane with a terminal olefin (CH$_2$=CHCH$_2$—OCH$_3$) is described in Warren K. Miller, et al. Inorganic Chemistry 2002, 41, 5453-5465.

The phosphine ligands (I) in which n and m are both 0 are additionally obtainable, for example, by reaction of monophosphine compounds of the general formula (XII) with alkyne compounds of the general formula (XIII) according to the following reaction equation 3 (RE 3), where R$^{17}$ in the formulae (XII) and (I) is as defined above for $R^{11}$, $R^{12}$, $R^{13}$, $R^{14}$, the preferences applying correspondingly. For $R^{15}$ and $R^{16}$ in formula (XIII), the definitions and preferences given for the phosphine ligand (I) apply correspondingly.

$$2(R^{17})_2PH + \underset{XII}{\overset{R^{15}}{\underset{R^{16}}{|||}}} \longrightarrow \underset{I}{\overset{R^{15}}{\underset{R^{16}}{\overset{R^{17}\ R^{17}}{\underset{R^{17}\ R^{17}}{P}}}}} \quad RE\ 3$$

The general reaction of monophosphine compounds with alkyne compounds is described in U.S. Pat. No. 3,681,481.

In a particularly preferred embodiment, the transition metal complexes used as catalysts comprise one (1) bidentate phosphine ligand of the general formula (I) and at least one monodentate monophosphine, ligand with at least one organic radical having 1 to 20 carbon atoms.

Denticity is understood in the context of the present invention to mean the number of bonds that the phosphine ligand can form to the central transition metal atom from one phosphorus atom of the phosphine ligand. In other words, monodentate phosphine ligands can form one bond from the phosphorus atom to the central transition metal atom; bidentate phosphine ligands can form two bonds from the phosphorus atoms to the central transition metal atom.

Preferred monodentate monophosphine ligands are monophosphine ligands of the general formula (Ia)

$$PR^{19}R^{20}R^{21} \quad (Ia)$$

in which $R^{19}$, $R^{20}$, $R^{21}$ are each independently unsubstituted or at least monosubstituted —$C_1$-$C_{20}$-alkyl, -phenyl, -benzyl, cyclohexyl or —($CH_2$)-cyclohexyl, where the substituents are selected from the group consisting of —$C_1$-$C_{20}$-alkyl, —F, —Cl, —Br, —OH, —$OR^a$, —COOH, —$COOR^a$, —$OCOR^a$, —CN, —$NH_2$, —$N(R^a)_2$ and —$NHR^a$;

$R^a$ is —$C_1$-$C_4$-alkyl.

The —$C_1$-$C_{20}$-alkyl may be linear or branched. Suitable radicals for $R^{19}$, $R^{20}$, $R^{21}$ include, for example, methyl, ethyl, 1-propyl, 2-propyl, 1-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, 1-tetradecyl, 1-pentadecyl, 1-hexadecyl, 1-heptadecyl, 1-octadecyl, 1-nonadecyl, 1-eicosyl, cyclopentyl, cyclohexyl, cycloheptyl and cyclooctyl, methylcyclopentyl, methylcyclohexyl, 1-(2-methyl)pentyl, 1-(2-ethyl)hexyl, 1-(2-propyl)heptyl and norbornyl.

Preference is given to monodentate monophosphine ligands (Ia) in which the three $R^{19}$, $R^{20}$, $R^{21}$ radicals are the same. Particular preference is given to monodentate monophosphine ligands (Ia) of the formula $P(n-C_qH_{2q+1})_3$ where q is 1 to 20, especially where q is 1 to 12. Most preferably, the monodentate monophosphine ligand (Ia) is selected from the group consisting of tri-n-butylphosphine, tri-n-hexylphosphine, tri-n-octylphosphine, tri-n-decylphosphine and tri-n-dodecylphosphine.

The transition metal complex used as a catalyst preferably comprises one bidentate phosphine ligand (I) and two monodentate monophosphine ligands (Ia), where the definitions and preferences given for the bidentate phosphine ligands (I) and the monodentate monophosphine ligands (Ia) apply correspondingly.

The transition metal complex may further comprise further ligands, examples of which include hydride, fluoride, chloride, bromide, iodide, formate, acetate, propionate, carboxylate, acetylacetonate, carbonyl, DMSO, hydroxide, trialkylamine, alkoxide.

The transition metal complexes used as catalysts can be produced either directly in their active form or proceeding from customary standard complexes, for example [M(p-cymene)$Cl_2]_2$, [M(benzene)$Cl_2]_n$, [M(COD)(allyl)], [M$Cl_3$× $H_2O$], [M(acetylacetonate)$_3$], [M(COD)$Cl_2]_2$, [M(DMSO)$_4Cl_2$] where M is an element from group 8, 9 or 10 of the Periodic Table, with addition of the corresponding phosphine ligand(s) only under reaction conditions in process stage (a) (in situ).

In the process according to the invention, the catalyst used is preferably at least one transition metal complex selected from the group consisting of

[Ru(P″$Bu_3$)$_2$(1,2-bis(ditetradecylphosphino)ethane)(H)$_2$],
[Ru(P″hexyl$_3$)$_2$(1,2-bis(ditetradecylphosphino)ethane)(H)$_2$],
[Ru(P″octyl$_3$)$_2$(1,2-bis(ditetradecylphosphino)ethane)(H)$_2$],
[Ru(P″decyl$_3$)$_2$(1,2-bis(ditetradecylphosphino)ethane)(H)$_2$],
[Ru(P″$Bu_3$)$_2$(1,2-bis(dipentadecylphosphino)ethane)(H)$_2$],
[Ru(P″hexyl$_3$)$_2$(1,2-bis(dipentadecylphosphino)ethane)(H)$_2$],
[Ru(P″octyl$_3$)$_2$(1,2-bis(dipentadecylphosphino)ethane)(H)$_2$],
[Ru(P″decyl$_3$)$_2$(1,2-bis(dipentadecylphosphino)ethane)(H)$_2$],
[Ru(P″$Bu_3$)$_2$(1,2-bis(dihexadecylphosphino)ethane)(H)$_2$],
[Ru(P″hexyl$_3$)$_2$(1,2-bis(dihexadecylphosphino)ethane)(H)$_2$],
[Ru(P″octyl$_3$)$_2$(1,2-bis(dihexadecylphosphino)ethane)(H)$_2$],
[Ru(P″decyl$_3$)$_2$(1,2-bis(dihexadecylphosphino)ethane)(H)$_2$],
[Ru(P″$Bu_3$)$_2$(1,2-bis(dioctadecylphosphino)ethane))(H)$_2$],
[Ru(P″hexyl$_3$)$_2$(1,2-bis(dioctadecylphosphino)ethane)(H)$_2$],
[Ru(P″octyl$_3$)$_2$(1,2-bis(dioctadecylphosphino)ethane)(H)$_2$],
[Ru(P″decyl$_3$)$_2$(1,2-bis(dioctadecylphosphino)ethane)(H)$_2$],
[Ru(P″$Bu_3$)(1,2-bis(ditetradecylphosphino)ethane)(CO)(H)$_2$],
[Ru(P″hexyl$_3$)(1,2-bis(ditetradecylphosphino)ethane)(CO)(H)$_2$],
[Ru(P″octyl$_3$) (1,2-bis(ditetradecylphosphino)ethane)(CO)(H)$_2$],
[Ru(P″decyl$_3$)(1,2-bis(ditetradecylphosphino)ethane)(CO)(H)$_2$],
[Ru(P″$Bu_3$)(1,2-bis(dipentadecylphosphino)ethane)(CO)(H)$_2$],
[Ru(P″hexyl$_3$)(1,2-bis(dipentadecylphosphino)ethane)(CO)(H)$_2$],
[Ru(P″octyl$_3$)(1,2-bis(dipentadecylphosphino)ethane)(CO)(H)$_2$],
[Ru(P″decyl$_3$)(1,2-bis(dipentadecylphosphino)ethane)(CO)(H)$_2$],
[Ru(P″$Bu_3$)(1,2-bis(dihexadecylphosphino)ethane)(CO)(H)$_2$],
[Ru(P″hexyl$_3$)(1,2-bis(dihexadecylphosphino)ethane)(CO)(H)$_2$],
[Ru(P″octyl$_3$)(1,2-bis(dihexadecylphosphino)ethane)(CO)(H)$_2$],
[Ru(P″decyl$_3$)(1,2-bis(dihexadecylphosphino)ethane)(CO)(H)$_2$],
[Ru(P″$Bu_3$)(1,2-bis(dioctadecylphosphino)ethane)(CO)(H)$_2$],
[Ru(P″hexyl$_3$)(1,2-bis(dioctadecylphosphino)ethane))(CO)(H)$_2$],
[Ru(P″octyl$_3$)(1,2-bis(dioctadecylphosphino)ethane)(CO)(H)$_2$],

[Ru(P″decyl$_3$)(1,2-bis(dioctadecylphosphino)ethane)(CO)(H)$_2$],
[Ru(P″Bu$_3$)(1,2-bis(ditetradecylphosphino)ethane)(CO)(H)(HCOO)],
[Ru(P″hexyl$_3$)(1,2-bis(ditetradecylphosphino)ethane)(CO)(H)(HCOO)],
[Ru(P″octyl$_3$)(1,2-bis(ditetradecylphosphino)ethane)(CO)(H)(HCOO)],
[Ru(P″decyl$_3$)(1,2-bis(ditetradecylphosphino)ethane)(CO)(H)(HCOO)],
[Ru(P″Bu$_3$)(1,2-bis(dipentadecylphosphino)ethane)(CO)(H)(HCOO)],
[Ru(P″hexyl$_3$)(1,2-bis(dipentadecylphosphino)ethane)(CO)(H)(HCOO)],
[Ru(P″octyl$_3$)(1,2-bis(dipentadecylphosphino)ethane)(CO)(H)(HCOO)],
[Ru(P″decyl$_3$)(1,2-bis(dipentadecylphosphino)ethane)(CO)(H)(HCOO)],
[Ru(P″Bu$_3$)(1,2-bis(dihexadecylphosphino)ethane)(CO)(H)(HCOO)],
[Ru(P″hexyl$_3$)(1,2-bis(dihexadecylphosphino)ethane)(CO)(H)(HCOO)],
[Ru(P″octyl$_3$)(1,2-bis(dihexadecylphosphino)ethane)(CO)(H)(HCOO)],
[Ru(P″decyl$_3$)(1,2-bis(dihexadecylphosphino)ethane)(CO)(H)(HCOO)],
[Ru(P″Bu$_3$)(1,2-bis(dioctadecylphosphino)ethane)(CO)(H)(HCOO)],
[Ru(P″hexyl$_3$)(1,2-bis(dioctadecylphosphino)ethane))(CO)(H)(HCOO)],
[Ru(P″octyl$_3$)(1,2-bis(dioctadecylphosphino)ethane)(CO)(H)(HCOO)] and
[Ru(P″decyl$_3$)(1,2-bis(dioctadecylphosphino)ethane)(CO)(H)(HCOO)].

With these, it is possible in the hydrogenation of carbon dioxide to achieve TOF values (turnover frequencies) of greater than 1000 h$^{-1}$ and partition coefficients $P_K$ greater than 100.

"Homogeneously catalyzed" is understood in the context of the present invention to mean that the catalyst is present at least partly dissolved in the liquid reaction medium. In a preferred embodiment, at least 90% of the catalyst used in process stage (a) is present dissolved in the liquid reaction medium, more preferably at least 95%, especially preferably more than 99%, the catalyst most preferably being present completely dissolved in the liquid reaction medium (100%), based in each case on the total amount of the catalyst present in the liquid reaction medium (liquid phases of the reaction mixture (Rg)).

The amount of the metal component in the transition metal complex used as the catalyst in process stage (a) is generally 0.1 to 5000 ppm by weight, preferably 1 to 800 ppm by weight and especially preferably 5 to 800 ppm by weight, based in each case on the overall liquid reaction mixture (Rg) in the hydrogenation reactor. The catalyst is preferably selected such that it is present enriched in the upper phase (U1), which means that the upper phase (U1) comprises the majority of the catalyst. "Enriched" and "majority" with regard to the catalyst are understood in the context of the present invention to mean a partition coefficient of the catalyst $P_K$=[concentration of the catalyst in the upper phase (U1)]/[concentration of the catalyst in the lower phase (L1)] of ≥10. Preference is given to a partition coefficient $P_K$ of ≥50 and particular preference to a partition coefficient $P_K$ of ≥100.

With the transition metal complexes used as catalysts, it is possible in the hydrogenation of carbon dioxide to achieve TOF values (turnover frequencies) of greater than 1000 h$^{-1}$.

(TON=mol of formic acid-amine adduct (A2) per mole of metal component in the catalyst based on the reaction time; TOF=mol of formic acid-amine adduct (A2) per mole of metal component in the catalyst per 1 hour of reaction time.) Turnover frequency (TOF) and turnover number TON; for definition of TOF and TON see: J. F. Hartwig, *Organotransition Metal Chemistry*, 1st edition, 2010, University Science Books, Sausalito/Calif. p. 545).

The present invention therefore also provides the transition metal complex and for the use thereof as a catalyst, especially as a catalyst in a process for preparing formic acid.

The present invention thus also provides a transition metal complex comprising at least one element selected from groups 8, 9 and 10 of the Periodic Table and at least one phosphine ligand of the general formula (I).

The present invention thus also provides a transition metal complex comprising a phosphine ligand of the general formula (I) and at least one monodentate phosphine ligand of the general formula (Ia).

The present invention thus also provides for the use of the transition metal complex as a catalyst in a process for preparing formic acid.

The hydrogenation of carbon dioxide in process stage (a) is effected in the liquid phase, preferably at a temperature in the range from 20 to 200° C. and a total pressure in the range from 0.2 to 30 MPa abs. The temperature is preferably at least 30° C. and especially preferably at least 40° C., and preferably at most 150° C., especially preferably at most 120° C. and very especially preferably at most 80° C. The total pressure is preferably at least 1 MPa abs and especially preferably at least 5 MPa abs, and preferably at most 20 MPa abs.

In a preferred embodiment, the hydrogenation in process stage (a) is effected at a temperature in the range from 40 to 80° C. and a pressure in the range from 5 to 20 MPa abs.

The partial pressure of carbon dioxide in process stage (a) is generally at least 0.5 MPa and preferably at least 2 MPa, and generally at most 8 MPa. In a preferred embodiment, the hydrogenation in process stage (a) is effected at a partial pressure of carbon dioxide in the range from 2 to 7.3 MPa.

The partial pressure of hydrogen in process stage (a) is generally at least 0.5 MPa and preferably at least 1 MPa, and generally at most 25 MPa and preferably at most 15 MPa. In a preferred embodiment, the hydrogenation in process stage (a) is effected at a partial pressure of hydrogen in the range from 1 to 15 MPa.

The molar ratio of hydrogen to carbon dioxide in the reaction mixture (Rg) in the hydrogenation reactor is preferably 0.1 to 10 and especially preferably 1 to 3.

The molar ratio of carbon dioxide to tertiary amine (A1) in the reaction mixture (Rg) in the hydrogenation reactor is preferably 0.1 to 10 and especially preferably 0.5 to 3.

The hydrogenation reactors used may in principle be any reactors which are suitable for gas/liquid reactions under the given temperature and the given pressure. Suitable standard reactors for gas-liquid reaction systems are specified, for example, in K. D. Henkel, "Reactor Types and Their Industrial Applications", in Ullmann's Encyclopedia of Industrial Chemistry, 2005,. Wiley-VCH Verlag GmbH & Co. KGaA, DOI: 10.1002/14356007.b04_087, chapter 3.3 "Reactors for gas-liquid reactions". Examples include stirred tank reactors, tubular reactors or bubble column reactors.

The hydrogenation of carbon dioxide in the process according to the invention can be performed batchwise or continuously. In batchwise mode, the reactor is charged with the desired liquid and any solid feedstocks and auxiliaries, and then carbon dioxide and the polar solvent are injected to the desired pressure at the desired temperature. After the end of the reaction, the reactor is generally decompressed and the two liquid phases formed are separated from one another. In continuous mode, the feedstocks and auxiliaries, including the carbon dioxide and the hydrogen, are added continuously. In a corresponding manner, the liquid phases are removed continuously from the reactor, such that the liquid level in the reactor remains constant on average. Preference is given to the continuous hydrogenation of carbon dioxide.

The mean residence time of the components present in the reaction mixture (Rg) in the hydrogenation reactor is generally 5 minutes to 5 hours.

In the homogeneously catalyzed hydrogenation, in process stage (a), a hydrogenation mixture (H) is obtained which comprises the catalyst, the polar solvent, the tertiary amine (A1) and the at least one formic acid-amine adduct (A2).

"Formic acid-amine adduct (A2)" is understood in the context of the present invention to mean either one (1) formic acid-amine adduct (A2) or mixtures of two or more formic acid-amine adducts (A2). Mixtures of two or more formic acid-amine adducts (A2) are obtained in process stage (a) when two or more tertiary amines (A1) are used in the reaction mixture (Rg) used.

In a preferred embodiment of the process according to the invention, a reaction mixture (Rg) is used in process stage (a) which comprises one (1) tertiary amine (A1) to obtain a hydrogenation mixture (H) comprising one (1) formic acid-amine adduct (A2).

In a particularly preferred embodiment of the process according to the invention, in process stage (a), a reaction mixture (Rg) is used which comprises, as the tertiary amine (A1), tri-n-hexylamine to obtain a hydrogenation mixture (H) which comprises the formic acid-amine adduct of tri-n-hexylamine and formic acid and corresponds to the following formula (A3)

$$N(n\text{-hexyl})_3 * x_i \, HCOOH \quad (A3).$$

In the formic acid-amine adduct of the general formula (A2), the $R^1, R^2, R^3$ radicals are each as defined above for the tertiary amine of the formula (A1), where the preferences mentioned there apply correspondingly.

In the general formulae (A2) and (A3), $x_i$ is in the range from 0.4 to 5. The factor $x_i$ gives the averaged composition of the formic acid-amine adduct (A2) or (A3), i.e. the ratio of bound tertiary amine (A1) to bound formic acid in the formic acid-amine adduct (A2) or (A3).

The factor $x_i$ can be determined, for example, by determining the formic acid content by acid-base titration with an alcoholic KOH solution using phenolphthalein. In addition, it is possible to determine the factor $x_i$ by determining the amine content by gas chromatography. The exact composition of the formic acid-amine adduct (A2) or (A3) depends on many parameters, for example the concentrations of formic acid and tertiary amine (A1), the pressure, the temperature and the presence and nature of further components, especially of the polar solvent.

Therefore, the composition of the formic acid-amine adduct (A2) or (A3), i.e. the factor $x_i$, can also vary over the individual process stages. For example, after removal of the polar solvent, a formic acid-amine adduct (A2) or (A3) with a relatively high formic acid content generally forms, the excess bound tertiary amine (A1) being released from the formic acid-amine adduct (A2) and forming a secondary phase.

In process stage (a), a formic acid-amine adduct (A2) or (A3) is generally obtained in which $x_i$ is in the range from 0.4 to 5, preferably in the range from 0.7 to 1.6.

The formic acid-amine adduct (A2) is present enriched in the lower phase (L1), i.e. the lower phase (L1) comprises the majority of the formic acid-amine adduct (A2). "Enriched" or "majority" with regard to the formic acid-amine adduct (A2) should be understood in the context of the present invention to mean a proportion by weight of the formic acid-amine adduct (A2) in the lower phase (L1) of >50% based on the total weight of the formic acid-amine adduct (A2) in the liquid phases (upper phase (U1) and lower phase (L1)) in the hydrogenation reactor.

Preferably, the proportion by weight of the formic acid-amine adduct (A2) in the lower phase (L1) is >70%, especially >90%, based in each case on the total weight of the formic acid-amine adduct (A2) in the upper phase (U1) and the lower phase (L1).

Workup of the Hydrogenation Mixture (H); Process Stage (b)

The hydrogenation mixture (H) obtained in the hydrogenation of carbon dioxide in process stage (a) preferably has two liquid phases, optionally after addition of water, and is subjected to further workup in process stage (b) according to one of steps (b1), (b2) or (b3).

Workup According to Process Stage (b1)

In a preferred embodiment, the hydrogenation mixture (H) is subjected to further workup according to step (b1).

In this case, the hydrogenation mixture (H) obtained in process stage (a) is subjected to further workup in a first phase separation apparatus by phase separation to obtain a lower phase (L1) comprising the formic acid-amine adduct (A2), the at least one polar solvent and residues of the catalyst, and an upper phase (U1) comprising the catalyst and the tertiary amine (A1).

Due to the distinct improvement in the partition coefficient ($P_k$) of the transition metal complex used as the catalyst compared to the prior art, the removal of the catalyst by phase separation is very substantially complete. The amount of the metal component of the catalyst present in the lower phase (L1) is generally less than 4 ppm by weight, preferably less than 3 ppm by weight, more preferably less than 2 ppm by weight and especially preferably less than or equal to 1 ppm by weight, based in each case on the lower phase (L1).

Residues of the catalyst can optionally be depleted further from the lower phase (L1) by subsequent extraction (workup according to process stage b3). Due to the distinct improvement in the partition coefficient ($P_K$), the removal of the transition metal compound used as the catalyst by phase separation is very substantially complete, and so it is possible to dispense with a subsequent extraction.

In a preferred embodiment, the upper phase (U1) is recycled to the hydrogenation reactor. The lower phase (L1), in a preferred embodiment, is supplied to the first distillation apparatus in process stage (c). It may also be advantageous to recycle any further liquid phase comprising unconverted carbon dioxide and present above the two liquid phases, and any gas phase comprising unconverted carbon dioxide and/or unconverted hydrogen, to the hydrogenation reactor. It may be desirable, for example, to discharge unwanted by-products or impurities by discharging a portion of the upper phase (U1) and/or a portion of the liquid or gaseous phases comprising carbon dioxide or carbon dioxide and hydrogen from the process.

The hydrogenation mixture (H) obtained in process stage (a) is generally separated by gravimetric phase separation. Suitable phase separation apparatuses are, for example, standard apparatuses and standard methods which can be found, for example, in E. Müller et al. "Liquid-liquid Extraction", in Ullman's Encyclopedia of Industrial Chemistry, 2005, Wiley-VCH Verlag GmbH & Co. KGaA, DOI: 10.1002/14356007.b93_06, chapter 3 "Apparatus".

The phase separation can be effected, for example, after decompression to about or close to atmospheric pressure and cooling of the liquid hydrogenation mixture, for example to about or close to ambient temperature.

In the context of the present invention, it has been found that, in the present system, i.e. a lower phase (L1) enriched with the formic acid-amine adducts (A2) and the polar solvent, and an upper phase (U1) enriched with the tertiary amine (A1) and the catalyst, the two liquid phases can also be separated from one another very efficiently even under a distinctly elevated pressure. Therefore, in the process according to the invention, the polar solvent and the tertiary amine (A1) are selected such that the separation of the lower phase (L1) enriched with the formic acid-amine adducts (A2) and the polar solvent from the upper phase (U1) enriched with tertiary amine (A1) and catalyst, and the recycling of the upper phase (U1) to the hydrogenation reactor, can be performed at a pressure of 1 to 30 MPa abs. According to the total pressure in the hydrogenation reactor, the pressure is preferably at most 20 MPa abs. Thus, it is possible, without prior decompression, to separate the two liquid phases (upper phase (U1) and lower phase (L1)) from one another in the first phase separation apparatus, and to recycle the upper phase (U1) to the hydrogenation reactor without a significant pressure increase.

It is also possible to perform the phase separation directly in the hydrogenation reactor. In this embodiment, the hydrogenation reactor simultaneously functions as the first phase separation apparatus, and process stages (a) and (b1) are both performed in the hydrogenation reactor. In this case, the upper phase (U1) remains in the hydrogenation reactor and the lower phase (L1) is supplied to the first distillation apparatus in process stage (c).

In one embodiment, the process according to the invention is performed in such a way that the pressure and the temperature in the hydrogenation reactor and in the first phase separation apparatus are the same or approximately the same, "approximately the same" being understood in the present case to mean a pressure difference of up to +/− 0.5 MPa or a temperature difference of up to +/− 10° C.

It has also been found that, surprisingly, in the present system, both liquid phases (upper phase (U1) and lower phase (L1)) can also be separated very efficiently from one another at elevated temperature, which corresponds to the reaction temperature in the hydrogenation reactor. In this respect, for phase separation in process stage (b1), there is also no requirement for cooling and subsequent heating of the upper phase (U1) to be recycled, which likewise saves energy.

Workup According to Process Stage (b3)

In a further preferred embodiment, the hydrogenation mixture (H) is subjected to further workup according to step (b3).

In this case, the hydrogenation mixture (H) obtained in process stage (a), as described above for process stage (b1), is separated in the first phase separation apparatus into the lower phase (L1) and the upper phase (U1), which is recycled to the hydrogenation reactor. In relation to the phase separation, the details and preferences given for process stage (b1) apply correspondingly to process stage (b3). In the case of the workup according to step (b3) too, it is possible to conduct the phase separation directly in the hydrogenation reactor. In this embodiment, the hydrogenation reactor simultaneously functions as the first phase separation apparatus. In that case, the upper phase (U1) remains in the hydrogenation reactor and the lower phase (L1) is supplied to the extraction unit.

The lower phase (L1) obtained after phase separation is subsequently subjected in an extraction unit to an extraction with a tertiary amine (A1) as an extractant for removal of the residues of the catalyst to obtain a raffinate (R2) comprising the formic acid-amine adduct (A2) and the at least one polar solvent, and an extract (E2) comprising the tertiary amine (A1) and the residues of the catalyst.

In a preferred embodiment, the extractant used is the same tertiary amine (A1) present in the reaction mixture (Rg) in process stage (a), such that the details and preferences given for process stage (a) in relation to the tertiary amine (A1) apply correspondingly to process stage (b3).

The extract (E2) obtained in process stage (b3), in a preferred embodiment, is recycled to the hydrogenation reactor in process stage (a). This enables efficient recovery of the catalyst. The raffinate (R2), in a preferred embodiment, is supplied to the first distillation apparatus in process stage (c).

Preferably, the extractant used in process stage (b3) is the tertiary amine (A1) which is obtained in the thermal dissociation unit in process stage (e). In a preferred embodiment, the tertiary amine (A1) obtained in the thermal dissociation unit in process stage (e) is recycled to the extraction unit in process stage (b3).

The extraction in process stage (b3) is effected generally at temperatures in the range from 0 to 150° C., preferably in the range from 30 to 100° C., and pressures in the range from 0.1 to 8 MPa. The extraction can also be performed under hydrogen pressure.

The extraction of the catalyst can be performed in any suitable apparatus known to those skilled in the art, preferably in countercurrent extraction columns, mixer-settler cascades or combinations of mixer-settler cascades and countercurrent extraction columns.

It may be the case that, as well as the catalyst, proportions of individual components of the polar solvent from the lower phase (L1) to be extracted are also dissolved in the extractant, the tertiary amine (A1). This is not a disadvantage for the process, since the amount of polar solvent already extracted need not be supplied to the solvent removal, and hence vaporization energy is saved under some circumstances.

Workup According to Process Stage (b2)

In a further preferred embodiment, the hydrogenation mixture (H) is subjected to further workup according to step (b2).

In this case, the hydrogenation mixture (H) obtained in process stage (a) is supplied entirely, without prior phase separation, directly to the extraction unit. In relation to the extraction, the details and preferences given for process stage (b3) apply correspondingly to process stage (b2).

In this case, the hydrogenation mixture (H) is subjected in an extraction unit to an extraction with a tertiary amine (A1) as an extractant for removal of the catalyst to obtain a raffinate (R1) comprising the formic acid-amine adduct (A2) and the at least one polar solvent, and an extract (E1) comprising the tertiary amine (A1) and the catalyst.

In a preferred embodiment, the extractant used is the same tertiary amine (A1) present in the reaction mixture (Rg) in process stage (a), such that the details and preferences given for process stage (a) in relation to the tertiary amine (A1) apply correspondingly to process stage (b2).

The extract (E1) obtained in process stage (b2), in a preferred embodiment, is recycled to the hydrogenation reactor in process stage (a). This enables efficient recovery of the catalyst. The raffinate (R1), in a preferred embodiment, is supplied to the first distillation apparatus in process stage (c).

Preferably, the extractant used in process stage (b2) is the tertiary amine (A1) which is obtained in the thermal dissociation unit in process stage (e). In a preferred embodiment, the tertiary amine (A1) obtained in the thermal dissociation unit in process stage (e) is recycled to the extraction unit in process stage (b2).

The extraction in process stage (b2) is effected generally at temperatures in the range from 0 to 150° C., preferably in the range from 30 to 100° C., and pressures in the range from 0.1 to 8 MPa. The extraction can also be performed under hydrogen pressure.

The extraction of the catalyst can be performed in any suitable apparatus known to those skilled in the art, preferably in countercurrent extraction columns, mixer-settler cascades or combinations of mixer-settler cascades and countercurrent extraction columns.

It may be the case that, as well as the catalyst, proportions of individual components of the polar solvent from the hydrogenation mixture (H) to be extracted are also dissolved in the extractant, the tertiary amine (A1). This is not a disadvantage for the process, since the amount of polar solvent already extracted need not be supplied to the solvent removal, and hence vaporization energy is saved under some circumstances.

Removal of the Polar Solvent; Process Stage (c)

In process stage (c), the polar solvent is removed from lower phase (L1), from the raffinate (R1) or from the raffinate (R2) in a first distillation apparatus. In the first distillation apparatus, a distillate (D1) and a biphasic bottoms mixture (B1) are obtained. The distillate (D1) comprises the polar solvent removed and, in a preferred embodiment, is recycled into the hydrogenation reactor in step (a). The bottoms mixture (B1) comprises the upper phase (U2) comprising the tertiary amine (A1), and the lower phase (L2) comprising the formic acid-amine adduct (A2). In one embodiment of the process according to the invention, in the first apparatus, in process stage (c), the polar solvent is partly removed, and so the bottoms mixture (B1) comprises as yet unremoved polar solvent. In process stage (c), it is possible to remove, for example, 5 to 98% by weight of the polar solvent present in the lower phase (L1), in the raffinate (R1) or in the raffinate (R2), preferably 50 to 98% by weight, more preferably 80 to 98% by weight and especially preferably 80 to 90% by weight, based in each case on the total weight of the polar solvent present in the lower phase (L1), in the raffinate (R1) or in the raffinate (R2).

In a further embodiment of the process according to the invention, in the first distillation apparatus, in process stage (c), the polar solvent is completely removed, "Completely removed" is understood in the context of the present invention to mean a removal of more than 98% by weight of the polar solvent present in the lower phase (L1), in the raffinate (R1) or in the raffinate (R2), preferably more than 98.5% by weight, especially preferably more than 99% by weight, especially more than 99.5% by weight, based in each case on the total weight of the polar solvent present in the lower phase (L1), in the raffinate (R1) or in the raffinate (R2).

The distillate (D1) removed in the first distillation apparatus, in a preferred embodiment, is recycled to the hydrogenation reactor in step (a).

The polar solvent can be removed from the lower phase (L1), the raffinate (R1) or the raffinate (R2), for example, in an evaporator or in a distillation unit consisting of evaporator and column, the column being filled with structured packings, random packings and/or trays.

The at least partial removal of the polar solvent is effected preferably at a bottom temperature at which, at the given pressure, no free formic acid is formed from the formic acid-amine adduct (A2). The factor $x_i$ of the formic acid-amine adduct (A2) in the first distillation apparatus is generally in the range from 0.4 to 3, preferably in the range from 0.6 to 1.8, especially preferably in the range from 0.7 to 1.7.

In general, the bottom temperature in the first distillation apparatus is at least 20° C., preferably at least 50° C. and especially preferably at least 70° C., and generally at most 210° C., preferably at most 190° C. The temperature in the first distillation apparatus is generally in the range from 20° C. to 210° C., preferably in the range from 50° C. to 190° C. The pressure in the first distillation apparatus is generally at least 0.001 MPa abs, preferably at least 0.005 MPa abs and especially preferably at least 0.01 MPa abs, and generally at most 1 MPa abs and preferably at most 0.1 MPa abs. The pressure in the first distillation apparatus is generally in the range from 0.0001 MPa abs to 1 MPa abs, preferably in the range from 0.005 MPa abs to 0.1 MPa abs and especially preferably in the range from 0.01 MPa abs to 0.1 MPa abs.

In the removal of the polar solvent in the first distillation apparatus, the formic acid-amine adduct (A2) and free tertiary amine (A1) may occur in the bottoms of first distillation apparatus, since the removal of the polar solvent gives rise to formic acid-amine adducts (A2) with relatively low amine content. This forms a bottoms mixture (B1) comprising the formic acid-amine adduct (A2) and the free tertiary amine (A1). The bottoms mixture (B1) comprises, depending on the amount of the polar solvent removed, the formic acid-amine adduct (A2) and possibly the free tertiary amine (A1) formed in the bottoms of the first distillation apparatus. The bottoms mixture (B1) is optionally subjected to further workup in process stage (d) for further workup, and then supplied to process stage (e). It is also possible to supply the bottoms mixture (B1) from process stage (c) directly to process stage (e).

In process stage (d), the bottoms mixture (B1) obtained in step (c) can be separated in a second phase separation apparatus into the upper phase (U2) and the lower phase (L2). The lower phase (L2) is subsequently subjected to further workup according to process stage (e). In a preferred embodiment, the upper phase (U2) from the second phase separation apparatus is recycled to the hydrogenation reactor in step (a). In a further preferred embodiment, the upper phase (U2) from the second phase separation apparatus is recycled to the extraction unit. For process stage (d) and the second phase separation apparatus, the details and preferences for the first phase separation apparatus apply correspondingly.

In one embodiment, the process according to the invention thus comprises steps (a), (b1), (c), (d) and (e). In a further embodiment, the process according to the invention comprises steps (a), (b2), (c), (d) and (e). In a further embodiment, the process according to the invention comprises steps (a), (b3), (c), (d) and (e). In a further embodiment, the process according to the invention comprises steps (a), (b1), (c) and (e). In a further embodiment, the process according to the invention comprises steps (a), (b2), (c) and (e). In a further embodiment, the process according to the invention comprises steps (a), (b3), (c) and (e).

In one embodiment, the process according to the invention consists of steps (a), (b1), (c), (d) and (e). In a further embodiment, the process according to the invention consists of steps (a), (b2), (c), (d) and (e). In a further embodiment, the process according to the invention consists of steps (a), (b3), (c), (d) and (e). In a further embodiment, the process according to the invention consists of steps (a), (b1), (c) and (e). In a further embodiment, the process according to the invention consists of steps (a), (b2), (c) and (e). In a further embodiment, the process according to the invention consists of steps (a), (b3), (c) and (e).

Dissociation of the Formic Acid-Amine Adduct (A2); Process Stage (e)

The bottoms mixture (B1) obtained according to step (c), or the lower phase (L2) obtained, optionally after the workup according to step (d), is supplied to a thermal dissociation unit for further conversion.

The formic acid-amine adduct (A2) present in the bottoms mixture (B1) and/or possibly in the lower phase (L2) is dissociated in the thermal dissociation unit to formic acid and the corresponding tertiary amine (A1).

The formic acid is discharged from the thermal dissociation unit. The tertiary amine (A1) is recycled to the hydrogenation reactor in step (a). The tertiary amine (A1) from the thermal dissociation reactor can be recycled directly to the hydrogenation reactor. It is also possible to recycle the tertiary amine (A1) from the thermal dissociation unit first to the extraction unit in process stage (b2) or process stage (b3) and then to pass it onward from the extraction unit to the hydrogenation reactor in step (a); this embodiment is preferred.

In a preferred embodiment, the thermal dissociation unit comprises a second distillation apparatus and a third phase separation apparatus, the formic acid-amine adduct (A2) being dissociated in the second distillation apparatus to obtain a distillate (D2) which comprises formic acid and is discharged (withdrawn) from the second distillation apparatus, and a biphasic bottoms mixture (B2) comprising an upper phase (U3), which comprises the tertiary amine (A1), and a lower phase (L3), which comprises the formic acid-amine adduct (A2).

The formic acid obtained in the second distillation apparatus can be withdrawn from the second distillation apparatus, for example, (i) overhead, (ii) overhead and via a side draw or (iii) only via a side draw. When the formic acid is withdrawn overhead, formic acid is obtained with a purity of up to 99.99% by weight. In the case of withdrawal via a side draw, aqueous formic acid is obtained, in which case particular preference is given here to a mixture comprising about 85% by weight of formic acid. According to the water content of the bottoms mixture (B1) supplied to the thermal dissociation unit or optionally to the lower phase (L2), the formic acid can be withdrawn to an enhanced degree as the top product, or to an enhanced degree via the side draw. If required, it is also possible to withdraw formic acid only via the side draw, preferably with a formic acid content of about 85% by weight, in which case the amount of water required can optionally also be established by adding additional water to the second distillation apparatus. The thermal dissociation of the formic acid-amine adduct (A2) is effected generally according to process parameters known from the prior art with regard to pressure, temperature and apparatus configuration. These are described, for example, in EP 0 181 078 or WO 2006/021 411. Suitable second distillation apparatuses are, for example, distillation columns, which generally comprise random packings, structured packings and/or trays.

In general, the bottom temperature in the second distillation apparatus is at least 130° C., preferably at least 140° C. and especially preferably at least 150° C., and generally at most 210° C., preferably at most 190° C., especially preferably at most 185° C. The pressure in the second distillation apparatus is generally at least 1 hPa abs, preferably at least 50 hPa abs and especially preferably at least 100 hPa abs, and generally at most 500 hPa, especially preferably at most 300 hPa abs and especially preferably at most 200 hPa abs.

The bottoms mixture (B2) obtained in the bottom of the second distillation apparatus is biphasic. In a preferred embodiment, the bottoms mixture (B2) is supplied to the third phase separation apparatus of the thermal dissociation unit and separated there into the upper phase (U3), which comprises the tertiary amine (A1), and the lower phase (L3), which comprises the formic acid-amine adduct (A2). The upper phase (U3) is discharged from the third phase separation apparatus of the thermal dissociation unit and recycled to the hydrogenation reactor in step (a). The recycling can be effected directly to the hydrogenation reactor in step (a), or the upper phase (U3) is supplied first to the extraction unit in step (b2) or step (b3) and passed onward thence to the hydrogenation reactor in step (a). The lower phase (L3) obtained in the third phase separation apparatus is then supplied again to the second distillation apparatus of the thermal dissociation unit. The formic acid-amine adduct (A2) present in the lower phase (L3) is then subjected in the second distillation apparatus to another dissociation to again obtain formic acid and free tertiary amine (A1) and to form, in the bottom of the second distillation apparatus of the thermal dissociation unit, another biphasic bottoms mixture (B2), which is then supplied again to the third phase separation apparatus of the thermal dissociation unit for further workup.

The bottoms mixture (B1) and/or optionally the lower phase (L2) can be supplied to the thermal dissociation unit in process stage (e) in the second distillation apparatus and/or the third phase separation apparatus. In a preferred embodiment, the bottoms mixture (B1) and/or optionally the lower phase (L2) is had into the second distillation apparatus of the thermal separation unit. In a further embodiment, the bottoms mixture (B1) and/or optionally the lower phase (L2) is fed into the third phase separation vessel of the thermal dissociation unit.

In a further embodiment, the bottoms mixture (B1) and/or optionally the lower phase (L2) is fed both into the second distillation apparatus of the thermal dissociation unit, and into the third phase separation apparatus of the thermal dissociation unit. For this purpose, the bottoms mixture (B1) and/or optionally the lower phase (L2) is divided into two substreams, in which case one substream is supplied to the second distillation apparatus and one substream to the third phase separation apparatus of the thermal dissociation unit.

The invention is illustrated by the drawings and examples which follow, without restricting it thereto.

Figure 2:
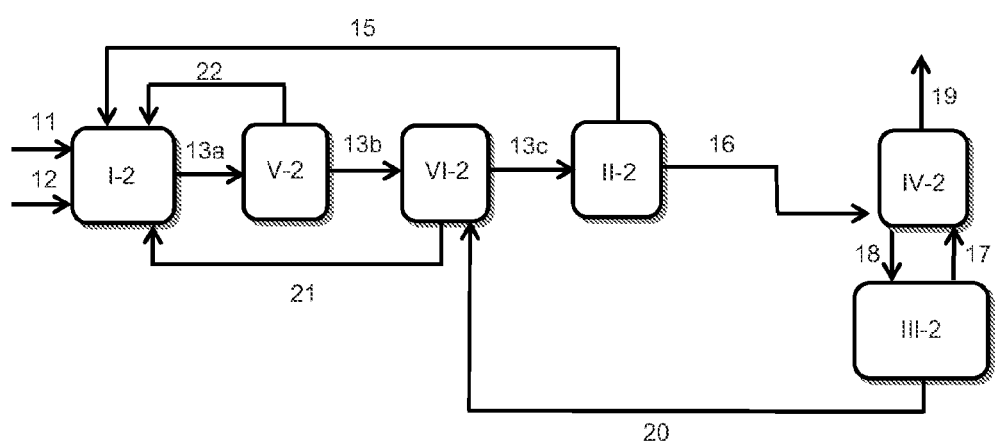

The individual drawings show:

FIG. 1 a block diagram of a preferred embodiment of the process according to the invention, FIG. 2 a block diagram of a further preferred embodiment of the process according to the invention.

In FIGS. 1 and 2, the reference numerals are defined as follows:

FIG. 1

I-1 hydrogenation reactor

II-1 first distillation apparatus

III-1 third phase separation apparatus (of the thermal dissociation unit)

IV-1 second distillation apparatus (of the thermal dissociation unit)

1 stream comprising carbon dioxide

2 stream comprising hydrogen

3 stream comprising formic acid-amine adduct ((A2), residues of the catalyst, polar solvent; (lower phase (L1))

5 stream comprising polar solvent; (distillate (D1))

6 stream comprising tertiary amine (A1) (upper phase (U2)) and formic acid-amine adduct (A2) (lower phase (L2)); bottoms mixture (B1)

7 stream comprising formic acid-amine adduct (A2); lower phase (L3)

8 stream comprising tertiary amine (A1) (upper phase (U3)) and formic acid-amine adduct (A2) (lower phase (L3)); bottoms mixture (B2)
9 stream comprising formic acid; (distillate (D2))
10 stream comprising tertiary amine (A1); upper phase (U3)
FIG. 2
I-2 hydrogenation reactor
II-2 first distillation apparatus
III-2 third phase separation apparatus (of the thermal dissociation unit)
IV-2 second distillation apparatus (of the thermal dissociation unit)
V-2 first phase separation apparatus
VI-2 extraction unit
11 stream comprising carbon dioxide
12 stream comprising hydrogen
13a stream comprising hydrogenation mixture (H)
13b stream comprising lower phase (L1)
13c stream comprising raffinate (R2)
15 stream comprising distillate (D1)
16 stream comprising bottoms mixture (B1)
17 stream comprising lower phase (L3)
18 stream comprising bottoms mixture (B2)
19 stream comprising formic acid; (distillate (D2))
20 stream comprising upper phase (U3)
21 stream comprising extract (E2)
22 stream comprising upper phase (U1)

In the embodiment according to FIG. 1, a stream 1 comprising carbon dioxide and a stream 2 comprising hydrogen are supplied to a hydrogenation reactor I-1. It is possible to supply further streams (not shown) to the hydrogenation reactor I-1, in order to compensate for any losses of the tertiary amine (A1) or of the catalyst which occur.

In the hydrogenation reactor I-1, carbon dioxide and hydrogen are converted in the presence of a tertiary amine (A1), of a polar solvent and of a transition metal complex as the catalyst. This affords a biphasic hydrogenation mixture (H) which comprises an upper phase (U1) comprising the catalyst and the tertiary amine (A1), and a lower phase (L1) comprising the polar solvent, residues of the catalyst and the formic acid-amine adduct (A2).

The lower phase (L1) is supplied as stream 3 to the distillation apparatus II-1. The upper phase (U1) remains in the hydrogenation reactor I-1. In the embodiment according to FIG. 1, the hydrogenation reactor I-1 functions simultaneously as the first phase separation apparatus.

In the first distillation apparatus II-1, the lower phase (L1) is separated into a distillate (D1) comprising the polar solvent, which is recycled as stream 5 to the hydrogenation reactor I-1, and into a biphasic bottoms mixture (B1) comprising an upper phase (U2), which comprises the tertiary amine (A1), and the lower phase (L2), which comprises the formic acid-amine adduct (A2).

The bottoms mixture (B1) is supplied as stream 6 to the third phase separation apparatus III-1 of the thermal dissociation unit.

In the third phase separation apparatus III-1 of the thermal dissociation unit, the bottoms mixture (B1) is separated to obtain an upper phase (U3), which comprises the tertiary amine (A1), and a lower phase (L3), which comprises the formic acid-amine adduct (A2).

The upper phase (U3) is recycled as stream 10 to the hydrogenation reactor I-1. The lower phase (L3) is supplied as stream 7 to the second distillation apparatus IV-1 of the thermal dissociation unit. The formic acid-amine adduct (A2) present in the lower phase (L3) is separated in the second distillation apparatus into formic acid and free tertiary amine (A1). In the second distillation apparatus IV-1, a distillate (D2) and a biphasic bottoms mixture (B2) are obtained.

The distillate (D2) comprising formic acid is discharged as stream 9 from the distillation apparatus IV-1. The biphasic bottoms mixture (B2) comprising the upper phase (U3), which comprises the tertiary amine (A1), and the lower phase (L3), which comprises the formic acid-amine adduct (A2), is recycled as stream 8 to the third phase separation apparatus III-1 of the thermal dissociation unit. In the third phase separation apparatus III-1, the bottoms mixture (B2) is separated into upper phase (U3) and lower phase (L3). The upper phase (U3) is recycled as stream 10 to the hydrogenation reactor I-1. The lower phase (L3) is recycled as stream 7 to the second distillation apparatus IV-1.

In the embodiment according to FIG. 2, a stream 11 comprising carbon dioxide and a stream 12 comprising hydrogen are supplied to a hydrogenation reactor I-2. It is possible to supply further streams (not shown) to the hydrogenation reactor I-2, in order to compensate for any losses of the tertiary amine (A1) or of the catalyst which occur.

In the hydrogenation reactor I-2, carbon dioxide and hydrogen are converted in the presence of a tertiary amine (A1), of a polar solvent and of an iron complex as the catalyst. This affords a biphasic hydrogenation mixture (H) which comprises an upper phase (U1) comprising the catalyst and the tertiary amine (A1), and a lower phase (L1) comprising the polar solvent, residues of the catalyst and the formic acid-amine adduct (A2).

The hydrogenation mixture (H) is supplied as stream 13a to a first phase separation apparatus V-2. In the first phase separation apparatus V-2, the hydrogenation mixture (H) is separated into the upper phase (U1) and the lower phase (L1).

The upper phase (U1) is recycled as stream 22 to the hydrogenation reactor I-2. The lower phase (L1) is supplied as stream 13b to the extraction unit VI-2. The lower phase (L1) is extracted therein with the tertiary amine (A1), which is recycled as stream 20 (upper phase (U3)) from the third phase separation apparatus III-2 to the extraction apparatus VI-2.

In the extraction unit VI-2, a raffinate (R2) and an extract (E2) are obtained. The raffinate (R2) comprises the formic acid-amine adduct (A2) and the polar solvent and is supplied as stream 13c to the first distillation apparatus II-2. The extract (E2) comprises the tertiary amine (A1) and the residues of the complex catalyst and is recycled as stream 21 to the hydrogenation reactor I-2.

In the first distillation apparatus II-2, the raffinate (R2) is separated into a distillate (D1) comprising the polar solvent, which is recycled as stream 15 to the hydrogenation reactor I-2, and into a biphasic bottoms mixture (B1).

The bottoms mixture (B1) comprises an upper phase (U2), which comprises the tertiary amine (A1), and a lower phase (L2), which comprises the formic acid-amine adduct (A2). The bottoms mixture (B1) is supplied as stream 16 to the second distillation apparatus IV-2.

The formic acid-amine adduct present in the bottoms mixture (B1) is separated in the second distillation apparatus IV-2 into formic acid and free tertiary amine (A1). In the second distillation apparatus IV-2, a distillate (D2) and a bottoms mixture (B2) are obtained.

The distillate (D2) comprising formic acid is discharged as stream 19 from the second distillation apparatus IV-2. The biphasic bottoms mixture (B2) comprising the upper phase (U3), which comprises the tertiary amine (A1), and the lower phase (L3), which comprises the formic acid-amine adduct (A2), is recycled as stream 18 to the third phase separation apparatus III-2 of the thermal dissociation unit.

In the third phase separation apparatus III-2 of the thermal dissociation unit, the bottoms mixture (B2) is separated to obtain an upper phase (U3) comprising the tertiary amine (A1), and a lower phase (L3) comprising the formic acid-amine adduct (A2).

The upper phase (U3) is recycled from the third phase separation apparatus III-2 as stream 20 to the extraction unit. The lower phase (L3) is supplied as stream 17 to the second distillation apparatus IV-2 of the thermal dissociation unit. The formic acid-amine adduct (A2) present in the lower phase (L3) is separated in the second distillation apparatus IV-2 into formic acid and free tertiary amine (A1). In the second distillation apparatus IV-2, as detailed above, another distillate (D2) and another bottoms mixture (B2) are obtained.

EXAMPLES

Synthesis of the Chelate Phosphine Ligands

Bis(dipentadecylphosphino)ethane: 250 ml of pentadecylmagnesium bromide (15% in tetrahydroluran (THF); 119 mmol) are initially charged in a 1|4-neck flask with internal thermometer, argon blanketing, metal/water condenser and stirrer, and cooled to −30° C. Subsequently, a solution of 5.5 g (23.8 mmol) of 1,2-bis(dichlorophosphino)-ethane in 100 ml of THF is added dropwise within 30 minutes, in the course of which a large amount of solids precipitates. The mixture is then warmed to room temperature within one hour and subsequently stirred at internal temperature 50° C. for a further 2 hours, which gives rise to a grayish-white suspension. This is admixed gradually, and while cooling with ice, with 95 ml of saturated and degassed $NH_4Cl$ solution to obtain a white suspension. Another 65 ml of degassed water are added thereto and the precipitate is filtered off with suction through a G2 frit under argon. The product is washed once with water and twice with 20 ml of THF, and dried under reduced pressure. This gives 22.2 g (93.5%) of the product in the form of a white powder. $^{31}P$ NMR ($CDCl_3$): −26.8 ppm (s); elemental analysis: calc. C 79.6%, H 13.8%, P 6.6%; exp. C 79.5%, H 14.0%, P 6.3%, Br 0.04%, Cl 0.06%, O<0.5%.

Bis(dioctadecylphosphino)ethane: 100 ml of octadecylmagnesium bromide (0.5 M in THF; mmol) are initially charged in a 1|4-neck flask with internal thermometer, argon blanketing, metal/water condenser and stirrer, and cooled to −30° C. Subsequently, a solution of 2.3 g (10 mmol) of 1,2-bis(dichloraphasphino)ethane in 100 ml of THF is added dropwise within 40 minutes, in the course of which a large amount of solids precipitates. The mixture is then warmed to room temperature within one hour and subsequently stirred at internal temperature 50° C. for a further 2 hours, which gives rise to a grayish-white suspension. This is admixed gradually, and while cooling with ice, with 50 ml of saturated and degassed $NH_4Cl$ solution to obtain a white suspension. Another 50 ml of degassed water are added thereto and the precipitate is filtered off with suction through a G2 frit under argon. The product is washed once with water and twice with 10 ml of THF, and dried under reduced pressure. This gives 11.0 g (88.0%) of the product in the form of a white powder. $^{31}P$ NMR ($CDCl_3$): −26.1 ppm (s).

The comparative examples (A1-a and A1-b) and the inventive examples (A2-a, A2-b, A3-a and A3-b)) demonstrate the hydrogenation of carbon dioxide ($CO_2$) and the reuse of the transition metal complex used as the catalyst.

A 100 ml or a 250 ml autoclave made of Hastelloy C (hydrogenation reactor), equipped with a paddle stirrer, was charged under inert conditions with the tertiary amine (A1), the polar solvent and the catalyst. Subsequently, the autoclave was closed and carbon dioxide was injected at room temperature. Thereafter, hydrogen ($H_2$) was injected and the reactor was heated while stirring (1000 rpm). After the reaction time, the autoclave was cooled and the hydrogenation mixture (H) decompressed, water was added and the mixture was stirred at room temperature for 10 minutes.

A biphasic hydrogenation mixture (H) was obtained, and the upper phase (U1) was enriched with the free tertiary amine (A1) and the catalyst, and the lower phase (L1) with the polar solvent and the formic acid-amine adduct (A2) formed.

The phases were subsequently separated. The formic acid content (in the form of the formic acid-amine adduct (A2)) of the lower phase (L1) and the ruthenium content ($C_{Ru}$) of both phases were determined by the methods described below. The upper phase (U1), comprising ruthenium catalyst, was then supplemented to 85 g with fresh tertiary amine (A1) and used again for $CO_2$ hydrogenation with the same solvent, under the same reaction conditions as above (see A1-b and A2-b). On completion of reaction and water addition, the lower phase (L1) was removed and admixed three times under inert conditions with the same amount (mass of amine corresponds to the mass of the lower phase) of fresh tertiary amine (A1) (stir at room temperature for 10 minutes and then separate phases) for catalyst extraction.

The total content of formic acid in the formic acid-amine adduct (A2) was determined potentiometrically by titration with 0.1N KOH in MeOH with a "Mettler Toledo DL50" titrator. The ruthenium content was determined by AAS. The parameters and results of the individual experiments are reported in table 1.

The comparative examples (A1-a and A1-b) and the inventive examples (A2-a, A2-b, A3-a and A3-b) show that the catalyst can be recycled into the $CO_2$ hydrogenation and reused there. The transition metal complexes used in accordance with the invention as catalysts can be depleted down to less than or equal to 1 ppm by phase separation alone.

TABLE 1

| | Comparative example A1-a (first hydrogenation) | Comparative example A1-b (reuse of the catalyst and extraction) | Inventive example A2-a (first hydrogenation) | Inventive example A2-b (reuse of the catalyst and extraction) |
|---|---|---|---|---|
| Tertiary amine (A1) | 85.0 g trihexylamine | upper phase from A1-a supplemented to 85 g with fresh trihexylamine | 85.0 g trihexylamine | upper phase from A2-a supplemented to 85.0 g with fresh trihexylamine |
| Polar solvent (used) | 25.0 g methanol 2.0 g water | 25.0 g methanol 2.0 g water | 25 0 g methanol 2.0 g water | 25.0 g methanol 2.0 g water |
| Catalyst | 0.34 g [Ru(Pnoctyl$_3$)$_4$(H)$_2$], 0.16 g 1,2-bis(didodecyl-phosphino)ethane | upper phase from A-1a | 0.34 g [Ru(Pnoctyl$_3$)$_4$(H)$_2$], 0.16 g 1,2-bis(dipentadecyl-phosphino)ethane | upper phase from A2-a |
| Injection of $CO_2$ | to 2.7 MPa abs | to 2.4 MPa abs | to 2.8 MPa abs | to 3.0 MPa abs |
| Injection of $H_2$ | to 12.20 MPa abs | to 11.9 MPa | to 12.0 MPa abs | to 11.7 MPa abs |

TABLE 1-continued

|  | Comparative example A1-a (first hydrogenation) | Comparative example A1-b (reuse of the catalyst and extraction) | Inventive example A2-a (first hydrogenation) | Inventive example A2-b (reuse of the catalyst and extraction) |
|---|---|---|---|---|
| Heating | 70° C. | 70° C. | 70° C. | 70° C. |
| Reaction time | 1.0 hour | 1.0 hour | 1.0 hour | 1.0 hour |
| Water addition after the reaction | 2.2 g | 2.1 g | 2.2 g | 2.1 g |
| Upper phase (U1) | 49.3 g | 54.5 g | 38.5 g | 53.7 g |
| Lower phase (L1) | 64.4 g | 58.5 g | 74.7 g | 58.9 g |
|  | 7.1% formic acid | 6.7% formic acid | 7.1% formic acid | 6.8% formic acid |
| $c_{Ru}$ upper phase (U1) after reaction and water addition | 250 ppm | 270 ppm | 280 ppm | 240 ppm |
| $c_{Ru}$ lower phase (L1) after reaction and water addition | 4 ppm | 5 ppm | 1 ppm | 1 ppm |

TABLE 2

|  | Inventive example A3-a (first hydrogenation) | Inventive example A3-b (reuse of the catalyst and extraction) |
|---|---|---|
| Tertiary amine (A1) | 85.0 g trihexylamine | 36.7 g upper phase from A3-a supplemented to 85 g with fresh trihexylamine |
| Polar solvent (used) | 25.0 g methanol 2.0 g water | 25.0 g methanol 2.0 g water |
| Catalyst | 0.32 g [Ru(PnOctyl$_3$)$_4$(H)$_2$], 0.22 g 1,2-bis(dioctadecyl-phosphino)ethane | upper phase from A-3a |
| Injection of CO$_2$ | to 2.3 MPa abs | to 2.4 MPa abs |
| Injection of H$_2$ | to 11.8 MPa abs | to 11.6 MPa |
| Heating | 70° C. | 70° C. |
| Reaction time | 1.0 hour | 1.0 hour |
| Water addition after the reaction | 2.2 g | 2.1 g |
| Upper phase (U1) | 41.0 g | 37.9 g |
| Lower phase (L1) | 75.0 g | 76.3 g |
|  | 8.8% formic acid | 7.8% formic acid |
| $c_{Ru}$ in upper phase (U1) after reaction and addition of water | 390 ppm | 310 ppm |
| $c_{Ru}$ in lower phase (L1) after reaction and addition of water | 2 ppm | 1 ppm |

The invention claimed is:

1. A process for preparing formic acid, comprising the steps of
   (a) homogeneously catalyzed reaction of a reaction mixture (Rg) comprising carbon dioxide, hydrogen, at least one polar solvent selected from the group consisting of methanol, ethanol, 1-propanol, 2-propanol, 1-butanol, 2-butanol, 2-methyl-1-propanol and water, and a tertiary amine of the general formula (A1)

$NR^1R^2R^3$ (A1)

in which
   $R^1$, $R^2$, $R^3$ are each independently an unbranched or branched, acyclic or cyclic, aliphatic, araliphatic or aromatic radical having in each case 1 to 16 carbon atoms, where individual carbon atoms may each independently also be substituted by a hetero group selected from the —O— and >N— groups, and two or all three radicals may also be joined to one another to form a chain comprising at least four atoms in each case,
   in the presence of at least one transition metal complex as a catalyst, comprising at least one element selected from groups 8, 9 and 10 of the Periodic Table and at least one phosphine ligand with at least one organic radical having at least 13 carbon atoms,
   in a hydrogenation reactor
   to obtain, optionally after addition of water, a biphasic hydrogenation mixture (H) comprising
      an upper phase (U1) comprising the catalyst and the tertiary amine (A1), and
      a lower phase (L1) comprising the at least one polar solvent, residues of the catalyst and a formic acid-amine adduct of the general formula (A2)

$NR^1R^2R^3 * x_i HCOOH$ (A2)

in which
   $x_i$ is in the range from 0.4 to 5 and
   $R^1$, $R^2$, $R^3$ are each as defined above,
   (b) workup of the hydrogenation mixture (H) obtained in step (a) according to one of the following steps:
      (b1) phase separation of the hydrogenation mixture (H) obtained in step (a) in a first phase separation apparatus into the upper phase (U1) and the lower phase (L1),
      or
      (b2) extraction of the catalyst from the hydrogenation mixture (H) obtained in step (a) in an extraction unit with an extractant comprising a tertiary amine (A1) to obtain
         a raffinate (R1) comprising the formic acid-amine adduct (A2) and the at least one polar solvent and
         an extract (E1) comprising the tertiary amine (A1) and the catalyst
      or
      (b3) phase separation of the hydrogenation mixture (H) obtained in step (a) in a first phase separation apparatus into the upper phase (U1) and the lower phase (L1) and extraction of the residues of the catalyst from the lower phase (L1) in an extraction unit with an extractant comprising a tertiary amine (A1) to obtain
         a raffinate (R2) comprising the formic acid-amine adduct (A2) and the at least one polar solvent and
         an extract (E2) comprising the tertiary amine (A1) and the residues of the catalyst, (c) separation of the at least one polar solvent from the lower phase (L1), from the raffinate (R1) or from the raffinate (R2) in a first distillation apparatus to obtain
a distillate (D1) comprising the at least one polar solvent, which is recycled into the hydrogenation reactor in step (a), and
a biphasic bottoms mixture (B1) comprising
an upper phase (U2) comprising the tertiary amine (A1), and a lower phase (L2) comprising the formic acid-amine adduct (A2),
(d) optional workup of the bottoms mixture (B1) obtained in step (c) by phase separation in a second phase separation apparatus into the upper phase (U2) and the lower phase (L2),
(e) dissociation of the formic acid-amine adduct (A2) present in the bottoms mixture (B1) and/or possibly in the lower phase (L2) in a thermal dissociation unit to obtain the corresponding tertiary amine (A1), which is recycled to the hydrogenation reactor in step (a), and formic acid, which is discharged from the thermal dissociation unit.

2. The process according to claim 1, wherein the transition metal complex used as the catalyst comprises at least one element selected from the group consisting of Ru, Rh and Pd, and at least one phosphine ligand with at least one organic radical having 13 to 30 carbon atoms, preferably having 14 to 26 carbon atoms, more preferably having 14 to 22 carbon atoms, especially preferably having 15 to 22 carbon atoms, especially having 16 to 20 carbon atoms.

3. The process according to claim 1, wherein the transition metal complex used as the catalyst comprises at least one bidentate phosphine ligand of the general formula (I)

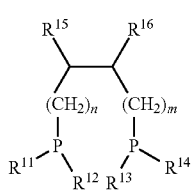

(I)

in which
$R^{11}, R^{12}, R^{13}, R^{14}$ are each independently unsubstituted or at least monosubstituted —$C_{13}$-$C_{30}$-alkyl, -(phenyl)-($C_7$-$C_{24}$-alkyl), -(phenyl)-($C_4$-$C_{24}$-alkyl)$_2$, -(phenyl)-($C_3$-$C_{24}$-alkyl)$_3$, -(phenyl)-(O—$C_7$-$C_{24}$-alkyl), -(phenyl)-(O—$C_4$-$C_{24}$-alkyl)$_2$, -(phenyl)-(O—$C_3$-$C_{24}$-alkyl)$_3$, -(cyclohexyl)-($C_7$-$C_{24}$-alkyl), -(cyclohexyl)-($C_4$-$C_{24}$-alkyl)$_2$, -(cyclohexyl)-($C_3$-$C_{24}$-alkyl)$_3$, -(cyclohexyl)-(O—$C_7$-$C_{24}$-alkyl), -(cyclohexyl)-(O—$C_4$-$C_{24}$-alkyl)$_2$ or -(cyclohexyl)-(O—$C_3$-$C_{24}$-alkyl)$_3$,
where the substituents are selected from the group consisting of —F, —Cl, —Br, —OH, —OR$^a$, —COOH, —COOR$^a$, —OCOR$^a$, —CN, —NH$_2$, —N(R$^a$)$_2$ and —NHR$^a$;
$R^{15}, R^{16}$ are each independently hydrogen or —$C_1$-$C_4$-alkyl or, together with the carbon atoms to which they are bonded, form an unsubstituted or at least monosubstituted phenyl or cyclohexyl ring,
where the substituents are selected from the group consisting of —OCOR$^a$, —OCOCF$_3$, —OSO$_2$R$^a$, —OSO$_2$CF$_3$, —CN, —OH, —OR$^a$, —N(R$^a$)$_2$, —NHR$^a$ and —$C_1$-$C_4$-alkyl;
R$^a$ is —$C_1$-$C_4$-alkyl and
n, m are each independently 0, 1 or 2.

4. The process according to claim 1, wherein the transition metal complex used as the catalyst comprises a bidentate phosphine ligand of the general formula (I) and at least one monodentate monophosphine ligand with at least one organic radical having 1 to 20 carbon atoms.

5. The process according to claim 1, wherein the monodentate monophosphine ligand has the general formula (Ia)

$$PR^{19}R^{20}R^{21} \qquad (Ia)$$

in which
$R^{19}, R^{20}, R^{21}$ are each independently unsubstituted or at least monosubstituted —$C_1$-$C_{20}$-alkyl, -phenyl, -benzyl, -cyclohexyl or —(CH$_2$)-cyclohexyl,
where the substituents are selected from the group consisting of —$C_1$-$C_{20}$-alkyl, —F, —Cl, —Br, —OH, —OR$^a$, —COOH, —COOR$^a$, —OCOR$^a$, —CN, —NH$_2$, —N(R$^a$)$_2$ and —NHR$^a$;
R$^a$ is —$C_1$-$C_4$-alkyl.

6. The process according to claim 1, wherein the bidentate phosphine ligand (I) is selected from the group consisting of 1,2-bis(ditetradecylphosphino)ethane, 1,2-bis(dipentadecylphosphino)ethane, 1,2-bis(dihexadecylphosphino)ethane and 1,2-bis(dioctadecylphosphino)ethane.

7. The process according to claim 1, wherein the monophosphine ligand (Ia) is selected from the group consisting of tri-n-butylphosphine, tri-n-hexylphosphine, tri-n-octylphosphine, tri-n-decylphosphine and tri-n-dodecylphosphine.

8. The process according to claim 1, wherein the tertiary amine used is a tertiary amine of the general formula (A1) in which the $R^1, R^2, R^3$ radicals are each independently selected from the group consisting of $C_5$— to $C_6$-alkyl, $C_5$— to $C_8$-cycloalkyl, benzyl and phenyl.

9. The process according to claim 1, wherein the tertiary amine (A1) used is tri-n-hexylamine.

10. The process according to claim 1, wherein the polar solvent used is water, methanol or a mixture of water and methanol.

11. The process according to claim 1, wherein the thermal dissociation unit comprises a second distillation apparatus and a third phase separation apparatus, and the formic acid-amine adduct (A2) is dissociated in the second distillation apparatus to obtain a distillate (D2) comprising formic acid, which is discharged from the second distillation apparatus, and a biphasic bottoms mixture (B2) comprising an upper phase (U3), which comprises the corresponding tertiary amine (A1), and a lower phase (L3), which comprises the formic acid-amine adduct (A2).

12. The process according to claim 11, wherein the bottoms mixture (B2) obtained in the second distillation apparatus is separated in the third phase separation apparatus of the thermal dissociation unit into the upper phase (U3) and the lower phase (L3), and the upper phase (U3) is recycled to the hydrogenation reactor in step (a) and the lower phase (L3) is recycled to the second distillation apparatus of the thermal dissociation unit.

13. A transition metal complex comprising at least one element selected from groups 8, 9 and 10 of the Periodic Table and at least one phosphine ligand of the general formula (I) according to claim 3, and at least one monodentate phosphine ligand of the general formula (Ia) according to claim 5.

14. The transition metal complex according to claim 13, which comprises a phosphine ligand of the general formula (I) according to claim 3 and at least one monodentate phosphine ligand of the general formula (Ia) according to claim 5.

15. A process comprising preparing formic acid in the presence of the transition metal complex according to claim 13.

16. A transition metal complex comprising at least one element selected from groups 8, 9, and 10 of the Periodic Table and at least one phosphine ligand of the general formula (I) according to claim 3, in which $R^{11}$, $R^{12}$, $R^{13}$, $R^{14}$ are each independently unsubstituted —$C_{15}$-$C_{22}$-alkyl, -(phenyl)-($C_7$-$C_{24}$-alkyl), -(phenyl)-($C_4$-$C_{24}$-alkyl)$_2$, -(phenyl)-($C_3$-$C_{24}$-alkyl)$_3$, -(phenyl)-(O—$C_7$-$C_{24}$-alkyl), -(phenyl)-(O—$C_4$-$C_{24}$-alkyl)$_2$, -(phenyl)-(O—$C_3$-$C_{24}$-alkyl)$_3$, -(cyclohexyl)-($C_7$-$C_{24}$-alkyl), -(cyclohexyl)-($C_4$-$C_{24}$-alkyl)$_2$, -(cyclohexyl)-($C_3$-$C_{24}$-alkyl)$_3$, -(cyclohexyl)-(O—$C_7$-$C_{24}$-alkyl), -(cyclohexyl)-(O—$C_4$-$C_{24}$-alkyl)$_2$ or -(cyclohexyl)-(O—$C_3$-$C_{24}$-alkyl)$_3$;

$R^{15}$, $R^{16}$ are each independently hydrogen or —$C_1$-$C_4$-alkyl or, together with the carbon atoms to which they are bonded, form an unsubstituted or at least monosubstituted phenyl or cyclohexyl ring, where the substituents are selected from the group consisting of —OCOR$^a$, —OCOCF$_3$, —OSO$_2$R$^a$, —OSO$_2$CF$_3$, —CN, —OH, —OR$^a$, —N(R$^a$)$_2$, —NHR$^a$ and -$C_1$-$C_4$-alkyl;

R$^a$ is —$C_1$-$C_4$-alkyl and n, m are each independently 0, 1 or 2.

* * * * *